US008126649B2

(12) United States Patent
Frasch et al.

(10) Patent No.: US 8,126,649 B2
(45) Date of Patent: Feb. 28, 2012

(54) METHODS FOR GENERATING A DISTRIBUTION OF OPTIMAL SOLUTIONS TO NONDETERMINISTIC POLYNOMIAL OPTIMIZATION PROBLEMS

(75) Inventors: Wayne Frasch, Phoenix, AZ (US); David Spetzler, Scottsdale, AZ (US); Justin York, Phoenix, AZ (US); Fusheng Xiong, Phoenix, AZ (US)

(73) Assignee: Arizona Board of Regents, a body corporate of the State of Arizona acting for and on behalf of Arizona State University, Scottsdale, AZ (US)

( * ) Notice: Subject to any disclaimer, the term of this patent is extended or adjusted under 35 U.S.C. 154(b) by 361 days.

(21) Appl. No.: 12/181,056

(22) Filed: Jul. 28, 2008

(65) Prior Publication Data

US 2009/0047677 A1 Feb. 19, 2009

Related U.S. Application Data

(63) Continuation-in-part of application No. PCT/US2007/002331, filed on Jan. 29, 2007.

(60) Provisional application No. 60/762,971, filed on Jan. 27, 2006.

(51) Int. Cl.

| | |
|---|---|
| ***G01N 33/48*** | (2006.01) |
| ***C12Q 1/68*** | (2006.01) |
| ***G06G 7/58*** | (2006.01) |

(52) U.S. Cl. .................. 702/11; 435/6; 702/20; 703/11

(58) Field of Classification Search ........................ None
See application file for complete search history.

(56) References Cited

U.S. PATENT DOCUMENTS

2005/0260574 A1 11/2005 Gibbs et al.

OTHER PUBLICATIONS

Yang et al., "A DNA solution of SAT problem by a modified sticker model", BioSystems, 2005, 81:1-9.

Lee et al., "Solving traveling salesman problems with DNA molecules encoding numerical values", BioSystems, 2004, 78:39-47.

*Primary Examiner* — Shubo Zhou

(74) *Attorney, Agent, or Firm* — Byrne Poh LLP; Nina R. Horan

(57) ABSTRACT

The present invention provides methods for generating a distribution of optimal answers to a nondeterministic polynomial optimization problem by providing a plurality of solutions comprising input polynucleotides, wherein each solution comprises identical input polynucleotides; and wherein the number of solutions comprising polynucleotides equals a number of data inputs in the problem to be answered, and wherein each input polynucleotide comprises an x segment and a y segment; providing a plurality of solutions comprising connection polynucleotides wherein each solution comprises identical connection polynucleotides; and wherein the number of solutions comprising connection polynucleotides equals a number of unique connections that can be made between the different data inputs, and wherein each polynucleotide in the set of connection polynucleotides is complementary to the x segment of one input polynucleotide and to the y segment of one different input polynucleotide; combining the solutions comprising the input polynucleotides with the solutions comprising the connection polynucleotides to form a hybridization mixture, wherein the combining is done under conditions to promote formation of hybridization complexes between complementary polynucleotides, and wherein each individual connection polynucleotide is added at a concentration based on a weighted value assigned to the individual connection polynucleotide; ligating the polynucleotides that are present in the hybridization complexes to form ligation products; and determining a concentration of the ligation products, wherein the ligation products present at the highest concentration represent optimal answers to the nondeterministic polynomial optimization problem.

12 Claims, 14 Drawing Sheets

WEIGHTS BASED UPON DISTANCE

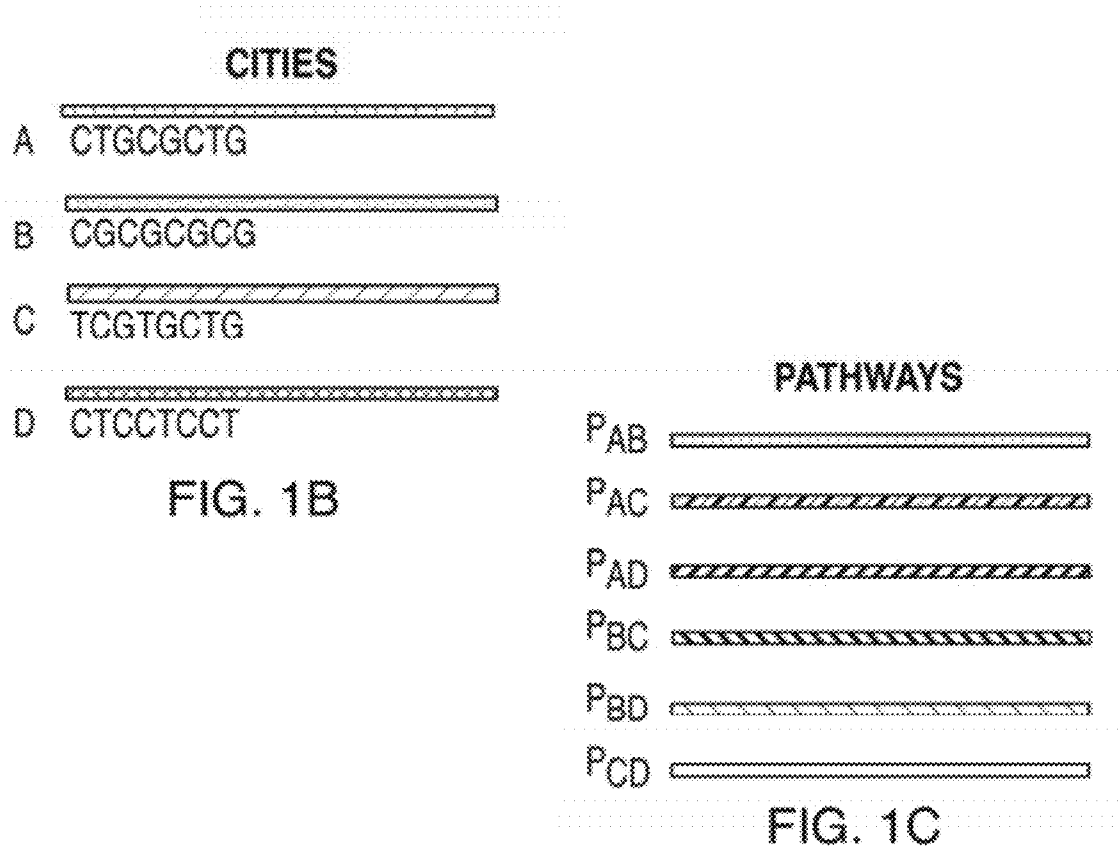
FIG. 1B
FIG. 1C
CITIES CONNECTED THROUGH PATHWAYS
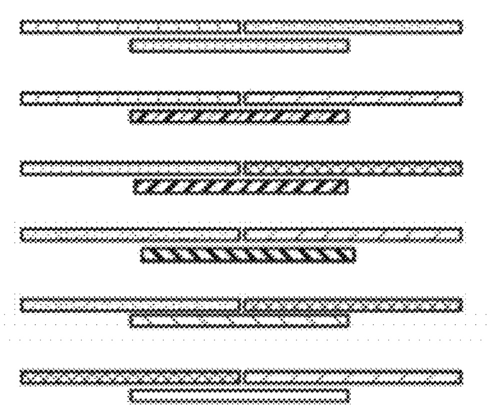
FIG. 1D

FIG. 4A
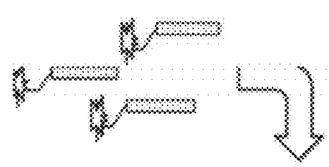
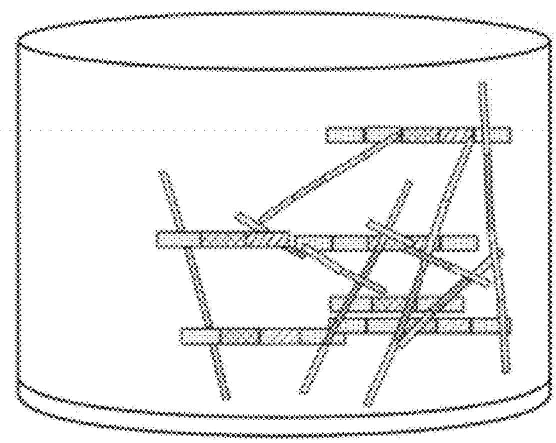
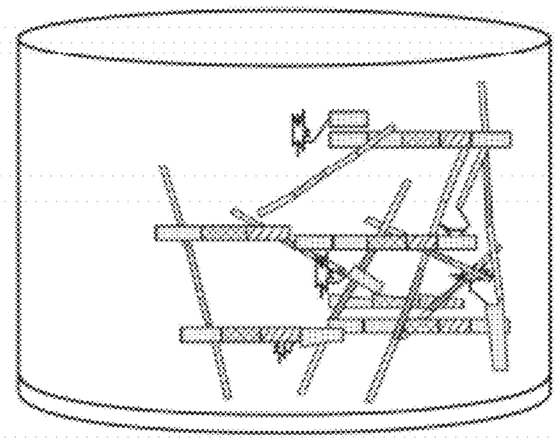
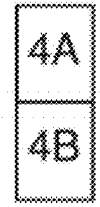
FIG. 4

The initial sequence for the starting and ending city A

CAATTCTAGTTCTCAACATT (SEQ ID NO: 13)

TGGCACGGGCGCGTCTCAACATT

New sequence for the starting city $A_s$ (SEQ ID NO: 14)

CAATTCTAGTCCCGCCGCCGGGTAG

New sequence for the ending city $A_e$ (SEQ ID NO: 15)

FIG. 9

METHODS FOR GENERATING A DISTRIBUTION OF OPTIMAL SOLUTIONS TO NONDETERMINISTIC POLYNOMIAL OPTIMIZATION PROBLEMS

RELATED APPLICATIONS

This application is a continuation in part of international application PCT/US2007/002331 with an international filing date of Jan. 29, 2007, which claims priority to U.S. Provisional Patent Application Ser. No. 60/762,971 filed Jan. 27, 2006, both of which are incorporated by reference herein in their entirety.

STATEMENT OF GOVERNMENT SUPPORT

The work disclosed herein was supported, at least in part, by DARPA/DSO grant AF9550-05-1-0424, and thus the U.S. government may have certain rights in the invention.

BACKGROUND OF THE INVENTION

Computing by representing information in the form of DNA base sequences enjoys several potential advantages over silicon-based computing methods, due to the massive parallelism of the biochemical reactions on DNA molecules. These advantages include significantly enhanced processing speeds, significantly reduced energy consumption, and significantly greater storage capacity. DNA computing can solve problems intractable by conventional computing methods including but not limited to organization of mass evacuations, organization of response to invasion, supply chain problems, and computer chip assembly problems. As a result, there is tremendous interest in utilizing the computing capacity of DNA A "nondeterministic polynomial optimization problem" is a class of optimization problems for which no efficient solution algorithm has been found. Tractable problems can be solved by computer algorithms that run in polynomial time; i.e., for a problem of size n, the time or number of steps needed to find the solution is a polynomial function of n. An optimization problem is called NP (nondeterministic polynomial) if its solution (if one exists) can be guessed and verified in polynomial time; nondeterministic means that no particular rule is followed to make the guess. Such "NP optimization problems" of any complexity thus pose a difficult computing issue, as previous attempts to solve using DNA-based computing require generation of the complete solution set. Thus, improved DNA-based computing methods for solving NP optimization problems are needed in the art.

SUMMARY OF THE INVENTION

In one aspect, the present invention provides methods for generating a distribution of optimal solutions to a nondeterministic polynomial optimization problem comprising:

(a) providing n input polynucleotides, wherein n equals a number of data inputs, and wherein each input polynucleotide:

(i) represents a unique data input; and (ii) comprises an x segment and a y segment;

(b) providing z connection polynucleotides, wherein z equals a number of unique connections that can be made between the different data inputs, and wherein each polynucleotide in the set of connection polynucleotides is complementary to the x segment of one input polynucleotide and to they segment of one different input polynucleotide;

(c) combining the input polynucleotides with the connection polynucleotides to form a mixture, wherein the combining is done under conditions to promote formation of hybridization complexes between complementary polynucleotides, and wherein each individual connection polynucleotide is added at a concentration based on a weight assigned to the individual connection polynucleotide;

(d) ligating input polynucleotides that are present in a hybridization complex to form ligation products; and (e) determining a concentration of the ligation products, wherein the ligation products present at the highest concentration represent optimal solutions to the nondeterministic polynomial optimization problem.

In one embodiment, step (c) comprises:

(i) combining all input polynucleotides only with those connection polynucleotides that are complementary to the x or y segment of a starting input polynucleotide to form a mixture, wherein the combining is done under conditions to promote hybridization between complementary polynucleotides to form a first hybridization complex between the starting input polynucleotide, a second input polynucleotide, and one connection polynucleotide; and (ii) combining all remaining connection polynucleotides not combined in step (i) with the mixture, wherein the combining is done under conditions to promote hybridization between complementary polynucleotides, wherein the remaining connection polynucleotides are added at a concentration based on a weight assigned to each individual remaining connection polynucleotide.

In another embodiment, step (c) comprises:

(i) combining all input polynucleotides only with those connection polynucleotides that are complementary to the x or y segment of at least two, but less than all, of the input polynucleotides, to form a mixture, wherein the combining is done under conditions to promote formation of hybridization complexes between complementary polynucleotides, and wherein each individual connection polynucleotide is added at a concentration based on a weight assigned to the individual connection polynucleotide; and (ii) combining all remaining connection polynucleotides not combined in step (i) with the mixture, wherein the combining is done under conditions to promote hybridization between complementary polynucleotides, wherein the remaining connection polynucleotides are added at a concentration based on a weight assigned to each individual remaining connection polynucleotide.

In various further embodiments described in more detail below, step (c)(ii) is repeated a desired number of times; the input polynucleotides are present in saturating concentration relative to the connection polynucleotides; determining a concentration of the ligation products comprises determining a length of the ligation products; the method comprises purifying those ligation products that contain each input polynucleotide prior to determining a concentration of the ligation products; determining a concentration of the ligation products comprises determining an order of polynucleotides in the ligation products; the detecting produces a reduced distance matrix with nonzero values only for those ligation products that exist in an optimal answer set; and the nondeterministic polynomial optimization problem is selected from the group consisting of evacuation planning, invasion response planning, supply chain problems, computer chip assembly, shortest path problems, graph theory problems, network design problems, sets and partitions problems, storage and retrieval problems, sequencing and scheduling problems, mathematical programming problems, algebra and number theory problems, and program optimization problems.

In another aspect, the present invention provides computer readable storage medium comprising a set of instructions for causing a processing device to execute procedures for carrying out the methods of the invention.

BRIEF DESCRIPTION OF THE FIGURES

FIG. 9 shows an exemplary two sequences that represented starting city $A_s$ and ending city $A_e$ separately designed to replace the single city A sequence. The second-half and the first-half of the original city A sequence were used in the new starting and ending sequences respectively.

FIG. 10(*b*) presents the order of cities in the single band shown in FIG. 9(*a*)(*c*) that start and stop at city A and also include each of the other 14 cities once and only once.

DETAILED DESCRIPTION OF THE INVENTION

Figure 1A:
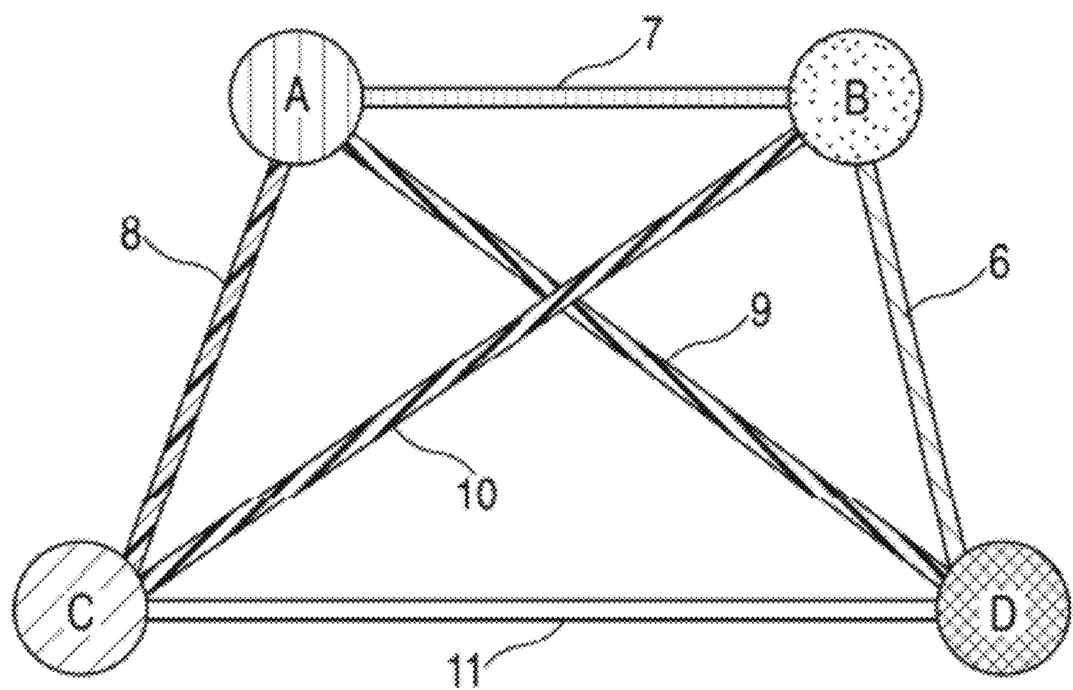
FIG. 1(A) General schematic of the traveling salesman problem; (B) example of how cities are defined as sequences; (C) List of pathways that exist in the graph; (D) How the pathway sequences bind to the city sequences; (E) How the ligation extends the sequences to form answers; (F) Example of a solution.

The present invention overcomes problems in prior art DNA-based computing methods for solving NP optimization problems, by providing methods that derive the most probable answers in a statistically significant manner that makes the methods scalable with increases in the number of data inputs, and thus makes the methods practical.

In one aspect, the present invention provides methods for generating a distribution of optimal solutions to a nondeterministic polynomial optimization problem comprising:

(a) providing n input polynucleotides, wherein n equals a number of data inputs, and wherein each input polynucleotide:

(i) represents a unique data input; and (ii) comprises an x segment and a y segment;

(b) providing z connection polynucleotides, wherein z equals a number of unique connections that can be made between the different data inputs, and wherein each polynucleotide in the set of connection polynucleotides is complementary to the x segment of one input polynucleotide and to they segment of one different input polynucleotide;

(c) combining the input polynucleotides with the connection polynucleotides to form a mixture, wherein the combining is done under conditions to promote formation of hybridization complexes between complementary polynucleotides, and wherein each individual connection polynucleotide is added at a concentration based on a weight assigned to the individual connection polynucleotide;

(d) ligating input polynucleotides that are present in a hybridization complex to form ligation products; and (e) determining a concentration of the ligation products, wherein the ligation products present at the highest concentration represent optimal solutions to the nondeterministic polynomial optimization problem.

A "nondeterministic polynomial optimization problem" is a class of optimization problems for which no efficient solution algorithim has been found (see, for example, the website www.cs.auc.dk/~luca/FS2INP-completeness). Tractable problems can be solved by computer algorithms that run in polynomial time; i.e., for a problem of size n, the time or number of steps needed to find the solution is a polynomial function of n. An optimization problem is called NP (nondeterministic polynomial) if its solution (if one exists) can be guessed and verified in polynomial time; nondeterministic means that no particular rule is followed to make the guess. Examples of such NP optimization problems are described below.

As used herein, a "distribution of optimal solutions" means one or more best solutions from the set of possible solutions. In one embodiment, the method identifies the most optimal solution, wherein the most optimal solution is the one represented by the ligation product present at the highest concentration. In a further embodiment, the method identifies the most probable answer, and the method further comprises determining the most optimal solution to the problem from this subset of most probable answers using conventional computing methods.

As used herein, "polynucleotide" means DNA, RNA, peptide nucleic acids ("PNA"), and locked nucleic acids ("LNA"), nucleic acid-like structures, as well as combinations thereof and analogues thereof. Nucleic acid analogues include known analogues of natural nucleotides which have similar or improved binding properties. "Analogous" forms of purines and pyrimidines are well known in the art, and include, but are not limited to aziridinylcytosine, 4-acetylcytosine, 5-fluorouracil, 5-bromouracil, 5-carboxymethylaminomethyl-2-thiouracil, 5-carboxymethylaminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5-methoxyuracil, 2-methylthio-N-6-isopentenyladenine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, and 2,6-diaminopurine. The oligonucleotides may also comprise nucleic acid backbone analogues including, but not limited to, phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs), methylphosphonate linkages or alternating methylphosphonate and phosphodiester linkages (Strauss-Soukup (1997) Biochemistry 36:8692-8698), and benzylphosphonate linkages, as discussed in U.S. Pat. No. 6,664,057; see also Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press).

The oligonucleotides may also contain analogous forms of ribose or deoxyribose as are well known in the art, including but not limited to 2' substituted sugars such as 2'-O-methyl-, 2'-fluoro- or 2'-azido-ribose, carbocyclic sugar analogs, α.-anomeric sugars, epimeric sugars such as arabinose, xyloses or lyxoses, pyranose sugars, sedoheptuloses, acyclic analogs and abasic nucleoside analogs such as methyl riboside. The oligonucleotides may also contain TNA (threose nucleic acid; also referred to as alpha-threofuranosyl oligonucleotides) (See, for example, Schong et al., Science 2000 Nov. 17, 290 (5495):1347-1351.)

The oligonucleotides may also comprise nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs), methylphosphonate linkages or alternating methylphosphonate and phosphodiester linkages (Strauss-Soukup (1997) Biochemistry 36:8692-8698), and benzylphosphonate linkages, as discussed in U.S. Pat. No. 6,664,057; see also Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press).

As used herein, "data inputs" are data points to be considered when solving any particular NP optimization problem. Each data input is represented by a unique input polynucleotide, and thus the number of input polynucleotides is equal to the number of unique data inputs. The limit on the number "n" of data inputs that can be processed using the methods of the invention is only limited by the number of unique sequences that can be designed.

As used herein, "x segment and y segment" are different portions of the input polynucleotides designed to provide for the required hybridization with the connection polynucleotides (ie, each polynucleotide in the set of connection polynucleotides is complementary to the x segment of one input polynucleotide and to the y segment of one different input polynucleotide). See, for example, FIG. 1D (input polynucleotides referred to as "cities" and connection polynucleotides referred to as "pathways" for purposes of the traveling salesman problem exemplified in the figure). There are no specific sequence requirements associated with an "x segment" versus a "y segment."

In one embodiment, each of the input polynucleotides and/or the connection polynucleotides is the same or similar length, and the x and y segments of each polynucleotide are of the same length. In another embodiment, the input polynucleotides and/or the connection polynucleotides are not the same length, but have similar melting temperatures. The input polynucleotides and/or the connection can comprise the x and y segments, or can consist of the x and y segments. In embodiments where the input polynucleotides and/or the connection polynucleotides comprise the x and y segments, the input polynucleotides and/or the connection polynucleotides can contain additional nucleotides either between the x and y segments, or at one or both termini of the input polynucleotide, most preferably where any additional nucleotides for the input polynucleotides are between the x and y segments, and where any additional nucleotides for the connection polynucleotides are at one or both termini of the connection polynucleotide. In one non-limiting example, additional nucleotides (such as GC-rich nucleotides) can be added at the terminus of one or more input nucleotides to increase their melting temperature relative to other input polynucleotides; this may be desirable, for example, in embodiments where a start and/or end input polynucleotide are known a priori (for example, in generating answers to the traveling salesman problem, as disclosed below), in order to reduce inappropriate insertion of starting and/or ending input polynucleotides inside the solutions.

The number of connection polynucleotides ("z") is equal to the number of unique connections that can be made between the different data inputs. The number of unique connections is equal to n*(n−1). The term "connection" refers to a link between data inputs.

Each individual connection polynucleotide is added to the mixture at a concentration based on a weight assigned to the individual connection polynucleotide. The weight assigned to individual connection polynucleotides differs depending on the NP optimization problem being solved and the specifics of the data inputs employed. Since the methods of the invention rely upon finding the optimal answer by identifying the sequences with the highest concentration, the method is fundamentally a maximization technique. Thus to solve a minimization problem it is most preferred to use a weighting function that inverses the relative weights. Any 1:1 function mapping of the parameters for a given input polynucleotide to sequence concentration of that input polynucleotide is acceptable.

For example, the weight assigned to a path between two cities may merely be a function of the distance between them. However, it could also include factors like the road conditions or the differential accessibility to fueling stations on different roads. As will be apparent to those of skill in the art, many such factors could influence the weight assigned to a specific connection polynucleotide. Identification of such factors, and determining how to weigh the connection polynucleotide based on those factors, is well within the level of those of skill in the art, based on the teachings herein. For example, for a shipping problem, the weight could be the cost of shipping plus the time of delivery, plus the number of times the package needs to be handled. For a map-covering problem, the weight could be calculated from the number of edges between vertices. Further non-limiting examples of weights that could be used are provided below.

As a result of the weighting, the methods of the invention generate solutions in concentrations proportional to their optimality. The methods thus find an optimal subset of all possible solutions. As a result, many poor solution sequences may not be formed since they occur with such low probability, and the methods result in an optimal subset of the possible solutions.

The method comprises combining the input polynucleotides with the connection polynucleotides to form a mixture, wherein the combining is done under conditions to promote formation of hybridization complexes between complementary polynucleotides. In a preferred embodiment, the input polynucleotides are added in saturating concentration. In a further embodiment, an automatic fluidic handling system is used to improve precision in amounts of the polynucleotides mixed together.

The specific hybridization conditions used will depend on the length of the polynucleotide probes employed, their GC content, as well as various other factors as is well known to those of skill in the art. (See, for example, Tijssen (1993) Laboratory Techniques in Biochemistry and Molecular Biology—Hybridization with Nucleic Acid Probes part I, chapt 2, "Overview of principles of hybridization and the strategy of nucleic acid probe assays," Elsevier, N.Y. ("Tijssen")).

The methods of the invention comprise ligating input polynucleotides that are present in a hybridization complex to form ligation products. An exemplary hybridization complex includes a single connection polynucleotide base-paired with an x segment from one input polynucleotide and also base paired with a y segment from a different input polynucleotide, thus juxtaposing two different input polynucleotides, which can then be ligated. The ligation can be accomplished by techniques known to those of skill in the art using commercially available nucleic acid ligases. Any nucleic acid ligase (depending on the nature of the polynucleotide) is suitable for use in the disclosed methods of the invention. Preferred ligases are those that preferentially form phosphodiester bonds at nicks in double-stranded DNA. That is, ligases that fail to ligate the free ends of single-stranded DNA at a significant rate are preferred. Thermostable ligases are especially preferred. Many suitable ligases are known, such as T4 DNA ligase (Davis et al., Advanced Bacterial Genetics—A Manual for Genetic Engineering (Cold Spring Harbor Laboratory, Cold Spring Harbor, N.Y., 1980)), *E. coli* DNA ligase (Panasnko et al., J. Biol. Chem. 253:4590-4592 (1978)), AMPLIGASE™ (Kalin et al., Mutat Res., 283(2):119-123 (1992); Winn-Deen et al., Mol Cell Probes (England) 7(3): 179-186 (1993)), Taq DNA ligase (Barany, Proc. Natl. Acad. Sci. USA 88:189-193 (1991), *Thermus thermophilus* DNA ligase (Abbott Laboratories), *Thermus scotoductus* DNA ligase and *Rhodothermus marinus* DNA ligase (Thorbjarnardottir et al., Gene 151:177-180 (1995)).

In one embodiment, the combining in step (b) of the methods of the invention comprises:

(i) combining all input polynucleotides only with those connection polynucleotides that are complementary to the x or y segment of a starting input polynucleotide to form a mixture, wherein the combining is done under conditions to promote hybridization between complementary polynucleotides to form a first hybridization complex between the starting input polynucleotide, a second input polynucleotide, and one connection polynucleotide; and (ii) combining all remaining connection polynucleotides not combined in step (i) with the mixture, wherein the combining is done under conditions to promote hybridization between complementary polynucleotides, wherein the remaining connection polynucleotides are added at a concentration based on a weight assigned to each individual remaining connection polynucleotide.

This embodiment is particularly useful for NP optimization problems where a starting data input is known, including but not limited to the shortest path problem, where a starting point in the path is known (see below).

In further examples of this embodiment, step (i) can comprise adding only those connection polynucleotides that are complementary to the x or y segment of two, three, or more, but less than all, of the input polynucleotides, followed by step (ii) as noted above. In a further embodiment, step (i) can comprise adding all but the ending input polynucleotide, where the ending input polynucleotide is known a priori (as, for example, in the traveling salesman problem).

In a further embodiment of each of these embodiments, step (ii) is repeated a desired number of times; in a further preferred embodiment, step (ii) is repeated (n−2) times.

In a further embodiment of each of these embodiments, step (i) is eliminated and step (ii) is repeated a desired number of times.

The methods of the invention also comprise determining a concentration of specific ligation products, wherein the ligation products present at the highest concentration represent optimal solutions to the nondeterministic polynomial optimization problem. This step involves identification of specific ligation products (ie: "solutions"), for which a concentration is then determined; ligation products present at the highest concentration represent optimal solutions to the problem. Such identification involves determining the order of oligonucleotides in the ligation product. Any method for determining the order of the polynucleotides in a given ligation product can be used, including but not limited to nucleic acid sequence analysis, polymerase chain reaction-based techniques, photoelectrochemical detection (for example, Gao and Tanzil, Nucleic Acids Res. 2005 Aug. 1; 33(13):e123.); quantum dot labeling (for example, Crut et al., Nucleic Acids Res. 2005 Jun. 20; 33(11):e98); multiplexed microsphere-based suspension array platforms (Dunbar, Clin Chim Acta. 2006 January; 363(1-2):71-82. Epub 2005 Aug. 15.); molecular beacons (Tsourkas et al., Nucleic Acids Res. 2003 Feb. 15; 31(4):1319-30.); molecular semaphores (WO 2005/080603); Bio-bar code PCR (for example, Nam et al., J Am Chem Soc. 2004 May 19; 126(19):5932-3), and DNA footprinting. In one embodiment a 3' biotinylated primer that is complementary to an input sequence is mixed with a 5' biotinylated primer that is complementary to another input. Ligase is used to link the two biotinylated primers together to form a detection complex, which can be detected using a molecular semaphore device, as disclosed in WO 2005/080603, incorporated by reference herein in its entirety. The antiparallel nature of DNA combined with the 3' and 5' labels allow the order of the input sequences to be determined.

Every possible input pairing (where an input pairing is a subset of a solution) is tested, $n^2$-n pairings, which results in a matrix with nonzero values only for those input pairings that exist in the optimal answer set, such that the more probable the pairing the higher the concentration. (See, for example, the Tables in the Examples) Thus, where no input pairings are detected, they will register as a "zero" value in the matrix.

The result is a reduced distance matrix with a searchable number of solutions (ie: ligation products), ~$n^3$ to $n^4$.

In a further embodiment, the sum of each row and column are equal, based on normalizing the amounts against the variation in the initial amount of probes added as well as variation in the gels, allowing the optimal solutions to be found by existing algorithms. A preferred embodiment is to use a maximum likelihood algorithm where the largest numbers are chosen sequentially to find the optimal solution.

Thus, all input pairings (ie: input polynucleotides plus connection polynucleotides) are possible, since all of the relevant polynucleotides are added, but that not all of the combinations will form; thus, the "reduced distance matrix" has zero values where that particular solution was not detected.

As will be understood by those of skill in the art, a reduced distance matrix is just one possibility for displaying results; any other suitable display technique can be used, including but not limited to simple lists or as the values between ordered pairs.

A preferred embodiment uses software to analyze the reduced distance matrix, determine the optimal solutions, and compute the exact cost to ensure that, of the likely paths found using the DNA computer, the best answer is chosen. (See, for example, FIG. 8)

Another embodiment uses the same primers to perform PCR, and determines the order of the input polynucleotides by the different sizes of the PCR products. Since the input polynucleotides are of a specific length, the answer sequences will occur in lengths that are proportional to the input length and the number of input polynucleotides between the two primers.

Determining a concentration of the individual ligated products can be accomplished by any means known to those of skill in the art, including but not limited to spectrophotometry, gel electrophoresis, surface plasmon resonance, fluorescence detection, radiation detection, and inducement of movement of the polynucleotides (see, for example, WO 2005/080603). In one embodiment, several cycles of amplification are performed, such as by ligase chain reaction ("LCR") to increase the number of copies of the ligated product in order to increase the ability to detect the product answers. Other techniques, such as PCR, can also be used to amplify the number of copies of the ligated products prior to determining the concentration of individual ligation products.

In one embodiment, determining the concentration of the ligation products includes determining the length of ligation products and the concentration of each ligation product based on length. In another embodiment, ligation products are purified prior to determination of their concentration. Any molecular separation technique can be used, including but not limited to any chromatography technique. In one embodiment, affinity columns are used with a biotinylated DNA probe that is the compliment of each input polynucleotide. The biotinylated probe is then attached to an avidin chromatography column to make the affinity column for that input polynucleotide. Thus, sequential affinity chromatography using separate affinity columns for the different input polynucleotides permits purification of individual ligation products that contain each input polynucleotides for which separate affinity chromatography was carried out, and other ligation products can be discarded. Thus, in one embodiment, ligation products that contain each of the input polynucleotides can be selected for. In combination with size selection, individual ligation products with, for example, a single copy of each input polynucleotide can be selected, and others discarded. Those of skill in the art will understand be able to implement various alternative embodiments based on the teachings herein.

In a further embodiment, avidin coated magnetic beads are used with a biotinylated DNA probe that is the compliment of each input polynucleotide. The biotinylated probe is then attached to an avidin bead to make the purification solution for that input polynucleotide. Thus, sequential purification solutions using separate tagged beads for the different input polynucleotides permits purification of ligation products that contain each input polynucleotide for which separate magnetic bead purification was carried out. Thus, in one embodiment, ligation products that contain each of the input polynucleotides can be selected for. In combination with size selection, ligation products with, for example, a single copy of each input polynucleotide can be selected. Those of skill in the art will understand be able to implement various alternative embodiments based on the teachings herein.

As discussed above, the methods of the invention can be used to solve any type of NP optimization problem, including but not limited to the following (see www.en.wikipedia.org/wiki/NP-complete, incorporated by reference herein in its entirety):

(A) Graph Theory Problems, Including but not Limited to

Covering and partitioning problems (including but not limited to the following problem types: vertex cover; dominating set; domatic number; graph k-colorability; achromatic number; monochromatic triangle; feedback vertex set; feedback arc set; partial feedback edge set; minimum maximal matching; partition into triangles; partition into isomorphic subgraphs; partition into Hamiltonian subgraphs; partition into forests; partition into cliques; partition into perfect matchings; two-stage maximum weight stochastic matching; covering by cliques; and covering by complete bipartite subgraphs);

Subgraphs and supergraphs problems (including but not limited to the following problem types: clique; independent set; induced subgraph with property Pi; induced connected subgraph with property Pi; induced path; balanced complete bipartite subgraph; bipartite subgraph; degree-bounded connected subgraph; planar subgraph; edge-subgraph; transitive subgraph; uniconnected subgraph; minimum k-connected subgraph; cubic subgraph; minimum equivalent digraph; Hamiltonian completion; interval graph completion; and path graph completion);

Vertex ordering problems (including but not limited to the following problem types: Hamiltonian circuit; directed Hamiltonian circuit; Hamiltonian path; bandwidth; directed bandwidth; optimal linear arrangement; directed optimal linear arrangement; minimum cut linear arrangement; rooted tree arrangement; directed elimination ordering; and elimination degree sequence);

Iso- and other morphisms problems (including but not limited to the following problem types: subgraph isomorphism; largest common subgraph; maximum subgraph matching; graph contractability; graph homomorphism; digraph D-morphism); path with forbidden pairs; multiple choice matching; graph Grundy numbering; kernel; K-closure; intersection graph basis; path distinguishers; metric dimension; Nesetril-Rödl dimension; threshold number; oriented diameter; and weighted diameter).

(B) Network Design Problems, Including but not Limited to

Spanning tree problems (including but not limited to the following problem types: degree constrained spanning tree; maximum leaf spanning tree; shortest total path length spanning tree; bounded diameter spanning tree; capacitated spanning tree; geometric capacitated spanning tree; optimum communication spanning tree; isomorphic spanning tree; Kth best spanning tree; bounded component spanning forest; multiple choice branching; Steiner tree; geometric Steiner tree; and cable trench);

Cuts and connectivity problems (including but not limited to the following problem types: graph partitioning; acyclic partition; max weight cut; minimum cut into bounded sets; biconnectivity augmentation; strong connectivity augmentation; network reliability; network survivability; multiway cut; and minimum k-cut);

Routing problems (including but not limited to the following problem types: bottleneck traveling salesman; Chinese postman for mixed graphs; Euclidean traveling salesman; K most vital arcs; Kth shortest path; metric traveling salesman; longest circuit; longest path; prize collecting traveling salesman; rural postman; shortest path in general networks; shortest weight-constrained path; stacker-crane; time constrained traveling salesman feasibility; traveling salesman; and vehicle routing);

Flow problems (including but not limited to the following problem types: minimum edge-cost flow; integral flow with multipliers; path constrained network flow; integral flow with homologous arcs; integral flow with bundles; undirected flow with lower bounds; directed two-commodity integral flow; undirected two-commodity integral flow; disjoint connecting paths; maximum length-bounded disjoint paths; maximum fixed-length disjoint paths); quadratic assignment problem; minimizing dummy activities in PERT networks; constrained triangulation; intersection graph for segments on a grid; edge embedding on a grid; geometric connected dominating set; minimum broadcast time; min-max multicenter; min-sum multicenter; uncapacitated facility location; and metric k-center);

(C) Sets and Partitions Problems, Including but not Limited to

Covering, hitting, and splitting problems (including but not limited to the following problem types: 3-dimensional matching; exact cover; set packing; set splitting; minimum cover; minimum test set; set basis; hitting set; intersection pattern; comparative containment; and 3-matroid intersection);

Weighted set problems (including but not limited to the following problem types: partition; subset sum; subset product; 3-partition; numerical 3-dimensional matching; numerical matching with target sums; expected component sum; minimum sum of squares; Kth largest subset; and Kth largest m-tuple);

(D) Storage and Retrieval Problems, Including but not Limited to

Data storage problems (including but not limited to the following problem types: bin packing; dynamic storage allocation; pruned trie space minimization; expected retrieval cost; rooted tree storage assignment; multiple copy file allocation; and capacity assignment);

Compression and representation problems (including but not limited to the following problem types: shortest common supersequence; shortest common superstring; longest common subsequence; bounded post correspondence problem; hitting string; sparse matrix compression; consecutive ones submatrix; consecutive ones matrix partition; consecutive ones matrix augmentation; consecutive block minimization; consecutive sets; 2-dimensional consecutive sets; string-to-string correction; grouping by swapping; external macro data compression; internal macro data compression; regular expression substitution; rectilinear picture compression; optimal vector quantization codebook; and minimal grammar-based compression);

Database problems (including but not limited to the following problem types: minimum cardinality key; additional key; prime attribute name; Boyce-Codd normal form violation; conjunctive query foldability; conjunctive boolean query; tableau equivalence; serializability of database histories; safety of database transaction systems; consistency of database frequency tables; and safety of file protection systems);

(E) Sequencing and Scheduling Problems, Including but not Limited to

Sequencing on one processor problems (including but not limited to the following problem types: sequencing with release times and deadlines; sequencing to minimize tardy tasks; sequencing to minimize tardy weight; sequencing to minimize weighted completion time; sequencing to minimize weighted tardiness; sequencing with deadlines and set-up times; and sequencing to minimize maximum cumulative cost);

Multiprocessor scheduling problems (including but not limited to the following problem types: multiprocessor scheduling; precedence constrained scheduling; resource constrained scheduling; scheduling with individual deadlines; preemptive scheduling; and scheduling to minimize weighted completion time);

Shop scheduling problems (including but not limited to the following problem types: open-shop scheduling; flow-shop scheduling; no-wait flow-shop scheduling; two-processor flow-shop with bounded buffer; and job-shop scheduling); timetable design problems; staff scheduling problems; production planning problems; and deadlock avoidance problems;

(F) Mathematical Programming Problems (Including but not Limited to the Following Problem Types:

integer programming; 0-1 Integer programming; quadratic programming; cost-parametric linear programming; feasible basis extension; minimum weight solution to linear equations; open hemisphere; K-relevancy; traveling salesman polytope non-adjacency; knapsack; integer knapsack; continuous multiple choice knapsack; partially ordered knapsack; and comparative vector inequalities);

(G) Algebra and Number Theory Problems, Including but not Limited to

Divisibility problems (including but not limited to the following problem types: quadratic congruences; simultaneous incongruences; simultaneous divisibility of linear polynomials; comparative divisibility; exponential expression divisibility; non-divisibility of a product polynomial; and non-trivial greatest common divisor);

Solvability of equations (including but not limited to the following problem types: quadratic diophantine equations; algebraic equations over GF[2]; root of modulus 1; number of roots for a product polynomial; periodic solution recurrence relation); permanent evaluation; cosine product integration; equilibrium point; unification with commutative operators; unification for finitely presented algebras; and integer expression membership);

Games and puzzles, including but not limited to generalized hex; generalized geography; generalized Kayles; sequential truth assignment; variable partition truth assignment; sift; alternating hitting set; alternating maximum weighted matching; annihilation; left-right Hackenbush for redwood furniture; square-tiling; crossword puzzle construction; generalized instant insanity; Minesweeper consistency problem; Sudoku™; Nurikabe™; paint by numbers; light up; Slither™ link; Clickomania™; Tetris™; and Mastermind™;

(J) Program Optimization, Including but not Limited to

Code generation problems (including but not limited to the following problem types: register sufficiency; feasible register assignment; register sufficiency for loops; code generation on a one-register machine; code generation with unlimited registers; code generation for parallel assignments; code generation with address expressions; code generation with unfixed variable locations; ensemble computation; and microcode bit optimization);

Program and scheme problems (including but not limited to the following problem types: inequivalence of programs with arrays; inequivalence of programs with assignments; inequivalence of finite memory programs; inequivalence of loop programs without nesting; inequivalence of simple functions; strong inequivalence of Ianov schemes; strong inequivalence for monadic recursion; non-containment for free B-schemes; non-freedom for loop-free program schemes; and programs with formally recursive procedures); cyclic ordering problems; non-liveness of free choice Petri net problems; reachability for 1-conservative Petri net problems; finite function generation problems; permutation generation problems; decoding of linear code problems; Shapley-Shubik voting power problems; clustering problems;

randomization test for matched pair problems; maximum likelihood ranking problems; matrix domination problems; matrix cover problems; simply deviated disjunction problems; decision tree problems; minimum weight and/or graph solution problems; fault detection in logic circuit problems; fault detection in directed graph problems; and fault detection with test point problems.

Further details of some of these NP optimization problems are presented below (taken from http://en.wikipedia.org/wiki/NP-complete; details of many of the other problems can also be found at this site):

Graph Theory

In mathematics and computer science, graph theory studies the properties of graphs. Informally, a graph is a set of objects called vertices (or nodes) connected by links called edges (or arcs) which can be directed (assigned a direction). Typically, a graph is designed as a set of dots (the vertices) connected by lines (the edges). Structures that can be represented as graphs are ubiquitous, and many problems of practical interest can be represented by graphs. The link structure of a website could be represented by a directed graph: the vertices are the web pages available at the website and there's a directed edge from page A to page B if and only if A contains a link to B. The development of algorithms to handle graphs is therefore of major interest in computer science.

A graph structure can be extended by assigning a weight to each edge. Graphs with weights can be used to represent many different concepts; for example if the graph represents a road network, the weights could represent the length of each road. Another way to extend basic graphs is by making the edges to the graph directional (A links to B, but B does not necessarily link to A, as in webpages), technically called a directed graph or digraph. A digraph with weighted edges is called a network.

Networks have many uses in the practical side of graph theory, network analysis (for example, to model and analyze traffic networks or to discover the shape of the internet).

Network analysis is the analysis of networks through network theory (or more generally graph theory). The networks may be social, transportation or virtual, such as the internet Analysis include descriptions of structure, such as small-world networks or scale-free networks, optimisation, such as Critical Path Analysis and PERT (Program Evaluation & Review Technique), and properties such as flow assignment.

Social network analysis maps relationships between individuals in social networks. Network analysis, and its close cousin traffic analysis, has significant use in intelligence. By monitoring the communication patterns between the network nodes, its structure can be established. This can be used for uncovering insurgent networks of both hierarchical and leaderless nature.

Link analysis is a subset of network analysis, exploring associations between objects. An example may be examining the addresses of suspects and victims, the telephone numbers they dialed and financial transactions they partaked in a given timeframe, and the familial relationships between these subjects as a part of police investigation. Link analysis here provides the crucial relationships and associations between very many objects of different types that are not apparent from isolated pieces of information. Computer-assisted or fully automatic computer-based link analysis is increasingly employed by banks and insurance agencies in fraud detection, by telecommunication operators in telecommunication network analysis, by medical sector in epidemiology and pharmacology, in law enforcement investigations, by search engines for relevance rating (and conversely by the spammers for spamdexing and by business owners for search engine optimization), and everywhere else where relationships between many objects have to be analyzed.

Centrality Measures

Information about the relative importance of nodes and edges in a graph can be obtained through centrality measures. For example, eigenvector centrality uses the eigenvectors of the adjacency matrix to determine nodes that tend to be frequently visited. An example is the page rank algorithm used by Google. The principal eigenvector of the modified adjacency matrix of the www-graph gives the page ranks as its components.

Fifteen puzzle: The n-puzzle is known in various versions, including the 8 puzzle, the puzzle, and with various names. It is a sliding puzzle that consists of a grid of numbered squares with one square missing, and the labels on the squares jumbled up. If the grid is 3×3, the puzzle is called the 8-puzzle or 9-puzzle. If the grid is 4×4, the puzzle is called the 15-puzzle or 16-puzzle. The goal of the puzzle is to un-jumble the squares by only making moves which slide squares into the empty space, in turn revealing another empty space in the position of the moved piece.

The n-puzzle is a classical problem for modelling algorithms involving heuristics. Commonly used heuristics for this problem include counting the number of misplaced tiles and finding the sum of the Manhattan distances between each block and its position in the goal configuration. Note that both are admissible, i.e., they never overestimate the number of moves left, which ensures optimality for certain search algorithms such as A*.

It is possible to use parity arguments to show that some starting positions for the n-puzzle are impossible to resolve, no matter how many moves are made. This is done by considering a function of the tile configuration that is invariant under any valid move, and then using this to partition the space of all possible labelled states into equivalence classes of reachable and unreachable states.

Knapsack problem: The knapsack problem is a problem in combinatorial optimization. It derives its name from the maximization problem of choosing as much as possible essentials that can fit into one bag (of maximum weight) you are going to carry on a trip. A similar problem very often appears in business, combinatorics, complexity theory, cryptography and applied mathematics. Given a set of items, each with a cost and a value, then determine the number of each item to include in a collection so that the total cost is less than some given cost and the total value is as large as possible.

The decision problem form of the knapsack problem is the question "can a value of at least Vbe achieved without exceeding the cost C?"

Hamiltonian cycle problem: In the mathematical field of graph theory the Hamiltonian path problem and the Hamiltonian cycle problem are problems of determining whether a Hamiltonian path or a Hamiltonian cycle exists in a given graph (whether directed or undirected). Both problems are NP-complete. The problem of finding a Hamiltonian cycle or path is in FNP.

There is a simple relation between the two problems. The Hamiltonian path problem for graph G is equivalent to the Hamiltonian cycle problem in a graph H obtained from G by adding a new vertex and connecting it to all vertices of G.

The Hamiltonian cycle problem is a special case of the traveling salesman problem, obtained by setting the distance between two cities to unity if they are adjacent and infinity otherwise.

Traveling salesman problem: Given a number of cities and the costs of traveling from any city to any other city, what is the cheapest round-trip route that visits each city once and then returns to the starting city?

An equivalent formulation in terms of graph theory is: Given a complete weighted graph (where the vertices would represent the cities, the edges would represent the roads, and the weights would be the cost or distance of that road), find the Hamiltonian cycle with the least weight.

It can be shown that the requirement of returning to the starting city does not change the computational complexity of the problem.

A related problem is the bottleneck traveling salesman problem (bottleneck TSP): Find the Hamiltonian cycle in a weighted graph with the minimal length of the longest edge.

The problem is of considerable practical importance, apart from evident transportation and logistics areas. A classic example is in printed circuit manufacturing: scheduling of a route of the drill machine to drill holes in a PCB. In robotic machining or drilling applications, the "cities" are parts to machine or holes (of different sizes) to drill, and the "cost of travel" includes time for retooling the robot (single machine job sequencing problem).

Clique problem: A clique (graph theory) in a graph is a set of pairwise adjacent vertices, or in other words, an induced subgraph which is a complete graph. In the graph at the right, vertices 1, 2 and 5 form a clique, because each has an edge to all the others. Then, the clique problem is the problem of determining whether a graph contains a clique of at least a given size k. Once we have located k or more vertices which form a clique, it's trivial to verify that they do, which is why the clique problem is in NP. The corresponding optimization problem, the maximum clique problem, is to find the largest clique in a graph Vertex cover problem: A vertex cover of an undirected graph G=(V,E) is a subset V of the vertices of the graph which contains at least one of the two endpoints of each edge:

$$V' \subseteq V : \forall \{a, b\} \in E : a \in V' \vee b \in V'.$$

The vertex cover problem is the optimization problem of finding a vertex cover of minimum size in a graph. The problem can also be stated as a decision problem:

INSTANCE: A graph G and a positive integer k.

QUESTION: Is there a vertex cover of size k or less for G?

Independent set problem: Given a graph G, an independent set is a subset of its vertices that are pairwise not adjacent. In other words, the subgraph induced by these vertices has no edges, only isolated vertices. Then, the independent set problem asks if, given a graph G and an integer k, does G have an independent set of size at least k? The corresponding optimization problem is the maximum independent set problem, which attempts to find the largest independent set in a graph.

Graph coloring problem: In graph theory, graph coloring is an assignment of "colors", almost always taken to be consecutive integers starting from 1 without loss of generality, to certain objects in a graph. Such objects can be vertices, edges, faces, or a mixture of the above. Among all, vertex coloring is the most important kind, not only because it is the starting point of the entire subject, but also because other coloring problems can be transformed into a vertex version. For example, an edge coloring of a graph is just the vertex coloring of its line graph. Likewise, a face coloring of a planar graph is just the vertex coloring of its (planar) dual. However, to keep things in their perspective, non-vertex coloring problems are usually stated and studied as are. Graph coloring enjoys many practical applications as well as theoretical challenges. Beside the classical types of problems, different limitations can also be set on the graph, or on the way a color is assigned, or even on the color itself. It has even reached popularity with the general public in the form of the popular number puzzle Sudoku. Graph coloring is still a very active field of research.

In another aspect, the present invention provides computer readable storage media comprising a set of instructions for causing a processing device to execute procedures for carrying out the methods of the invention disclosed above. The computer readable storage medium can include, but is not limited to, magnetic disks, optical disks, organic memory, and any other volatile (e.g., Random Access Memory ("RAM")) or non-volatile (e.g., Read-Only Memory ("ROM")) mass storage system readable by a central processing unit ("CPU"). The computer readable storage medium includes cooperating or interconnected computer readable medium, which can exist exclusively on the processing system of the processing device or be distributed among multiple interconnected processing systems that may be local or remote to the processing device.

In a preferred embodiment, the computer readable storage medium comprises a set of instructions for causing a processing device (such as a computer) to execute the methods of the invention. In one embodiment, the process is completely automated, wherein a user selects input and connection oligonucleotide sequences; the computer readable storage medium thus provides instructions to a processing device to cause a nucleic acid synthesizer to effect synthesis of the input and connection oligonucleotides. The user provides parameters for combining of the input and connection polynucleotides; the computer readable storage medium thus provides instructions to a processing device to cause, for example, an automated microplate system comprising a robotic arm to automatically carry out the desired combinations under the desired conditions, including ligation. The computer readable storage medium further provides instructions to a processing device to cause a device to identify individual oligonucleotide products and determine their concentration, wherein the ligation products present at the highest concentration represent optimal solutions to the nondeterministic polynomial optimization problem. Embodiments of the instructions include all of those discussed above for the methods of the invention.

In another embodiment, only certain portions of the method are automated.

Figure 7:
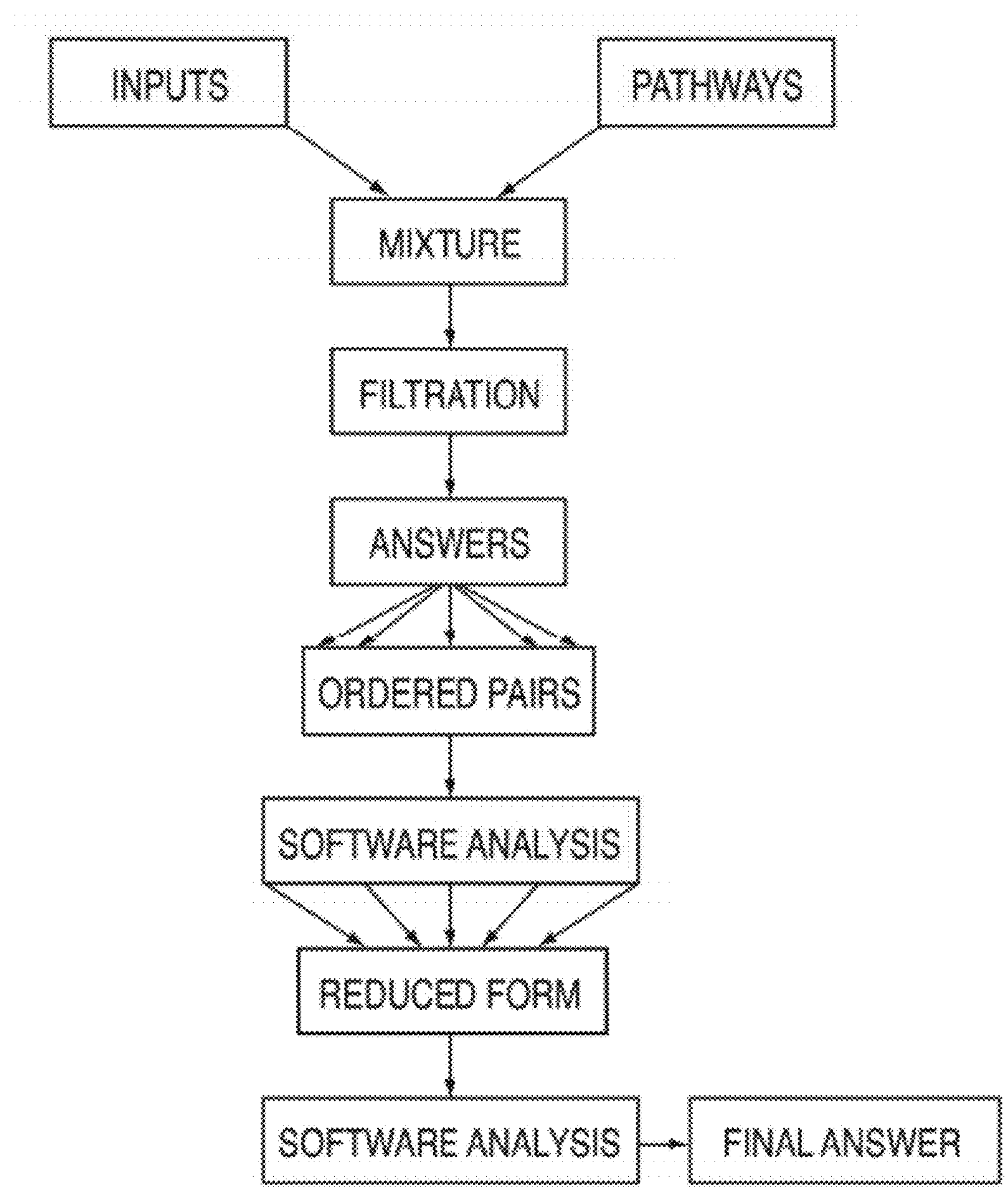
FIG. 7 shows an exemplary flow chart for an automated embodiment of the methods of the invention.

FIG. 7 provides an exemplary flow chart for one such embodiment. For example, the computer readable storage medium provides instructions for causing a processing device to determine a reduced distance matrix from a set of ordered pairs, as disclosed above. The computer readable storage medium may further provide instructions for causing a processing device to analyze the reduced distance matrix, determine the optimal solutions, and compute the exact cost to ensure that, of the likely paths found using the DNA computer, the best answer is chosen. It will be understood by those of skill in the art that all of these steps after ordered pair analysis are optional and are not necessary wherein ordered pair analysis can be performed by visual inspection, as in Example 3 below.

The present invention may be better understood with reference to the accompanying examples, which are intended for purposes of illustration only and should not be construed to limit the scope of the invention.

EXAMPLE 1

General Methodology to Solve the Traveling Salesman Problem

Step 1: Create a Set of Unique DNA Sequences for Each City ("Input Polynucleotides" or "City Sequences") and for Each Path that Connects Cities ("Connection Polynucleotides" or "Pathway Sequences")

Figures 1E, 1F:
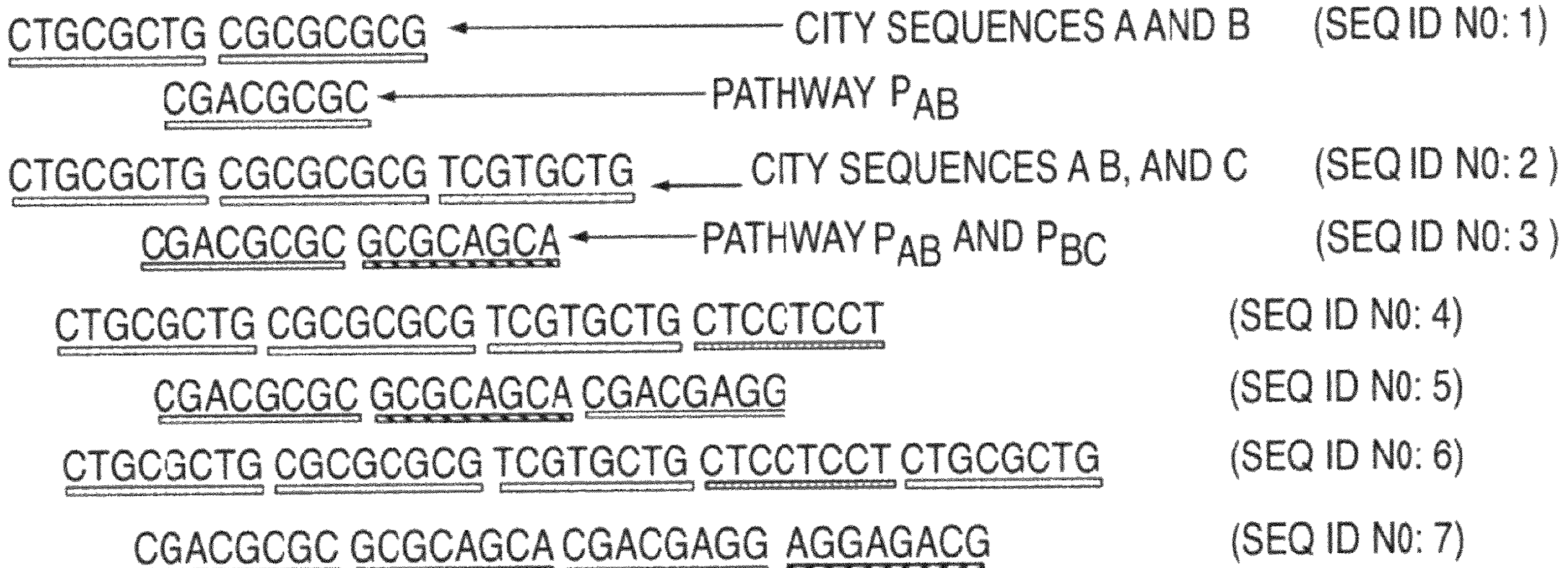
Figure 2:
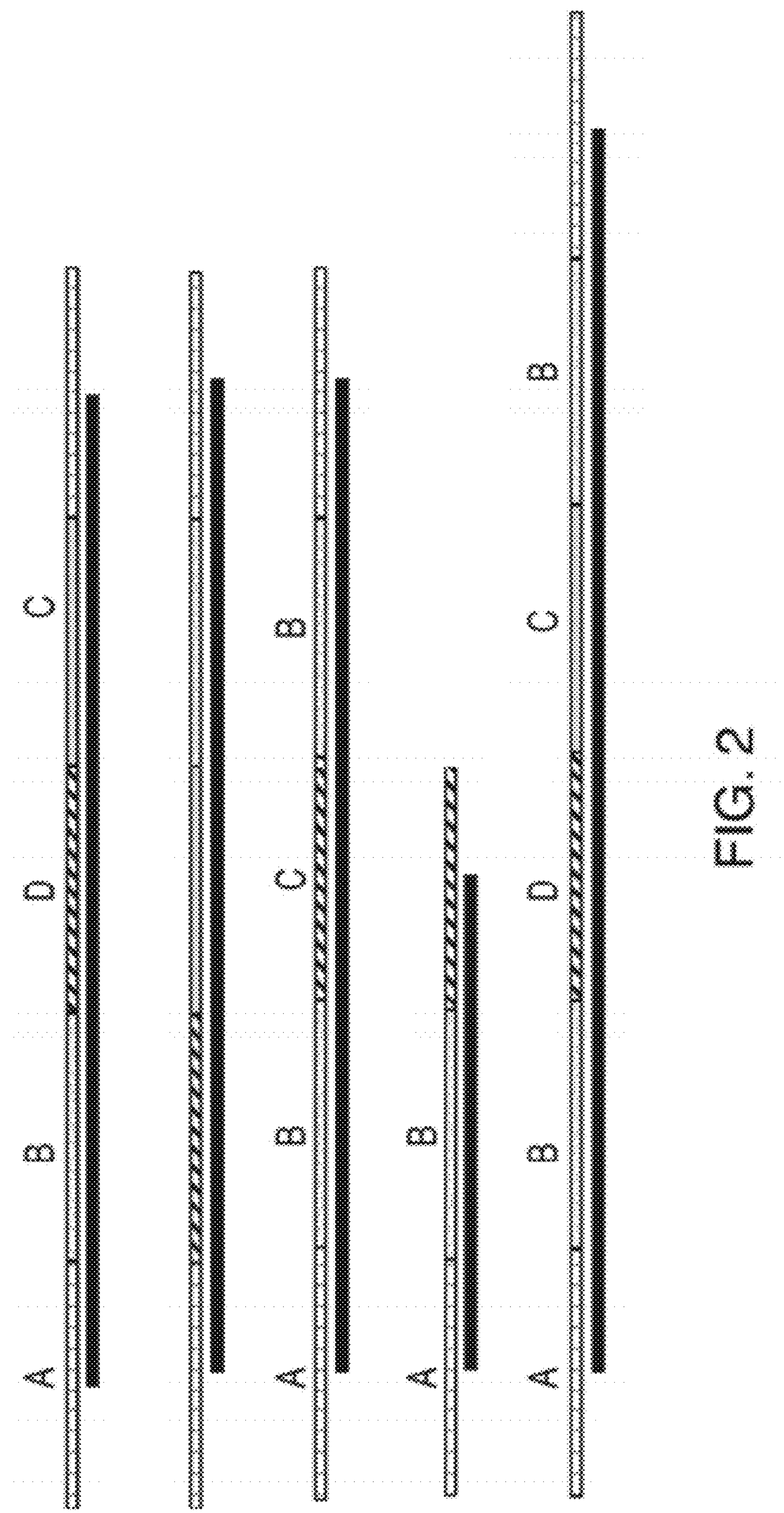
FIG. 2 shows the product of the ligation step.

In this example, 20 base pair nucleotides that correspond to each vertex (city) in the graph (city sequences) are prepared (FIGS. 1A and 1B). FIG. 1 corresponds to a 4 city problem for the purpose of illustration of the concept. Additionally, 20-mer sequences are created to represent the edges (pathway sequences) in the graph (FIG. 1C). If two city sequences, A and B, are composed of two 10-mer sequences $x_1y_1$ and $x_2y_2$ (ie: each of the "x" and "y" portions are 10 nucleotides in length), then an edge or path, $P_{AB}$, from A to B is a 20-mer composed of the Watson-Crick complement of $y_1$ and $x_2$ ($y_1x_2$). Thus, when put in solution, the path sequence binds to the second half of the source city and the first half of the destination city, serving as a connector for binding the cities together (FIGS. 1D and 1E).

Step 2: Hybridize City and Pathway DNA Sequences Based on a Distance Matrix Between Cities.

City sequences are added in saturating amounts to the hybridization mix while the limiting amounts of pathway sequences are determined by the distance matrix. This generates DNA strands that incorporate some or all of the cities. Optimal paths through the graph are generated by combining many copies of the city sequences and various concentrations of pathway sequences into a solution and letting them hybridize (FIG. 1F), and ligating the products. The most probable order that the cities should be visited for greatest efficiency are made in the highest concentrations, and many poor solution sequences may not be formed since they occur with such low probability. Since only some of the best solutions are generated, it is not necessary to start with enough DNA to generate all possible answers; this eliminates the staggering amount of DNA needed to compute all possible solutions to problems with more than 20 cities. This allows us to generate an optimal subset of all possible solutions, avoiding scalability problems identified in the art.

Step 3: Removal of Answer Sequences ("Ligation Products") Lacking a City Sequence.

An answer sequence is clearly incorrect if one or more of the city sequences is longer or shorter than the length defined by the number of cities. For the 10 city problem, this results in 220 base pair DNA oligomers, as each answer starts and end with City A and each city is a 20mer.

Figure 3:
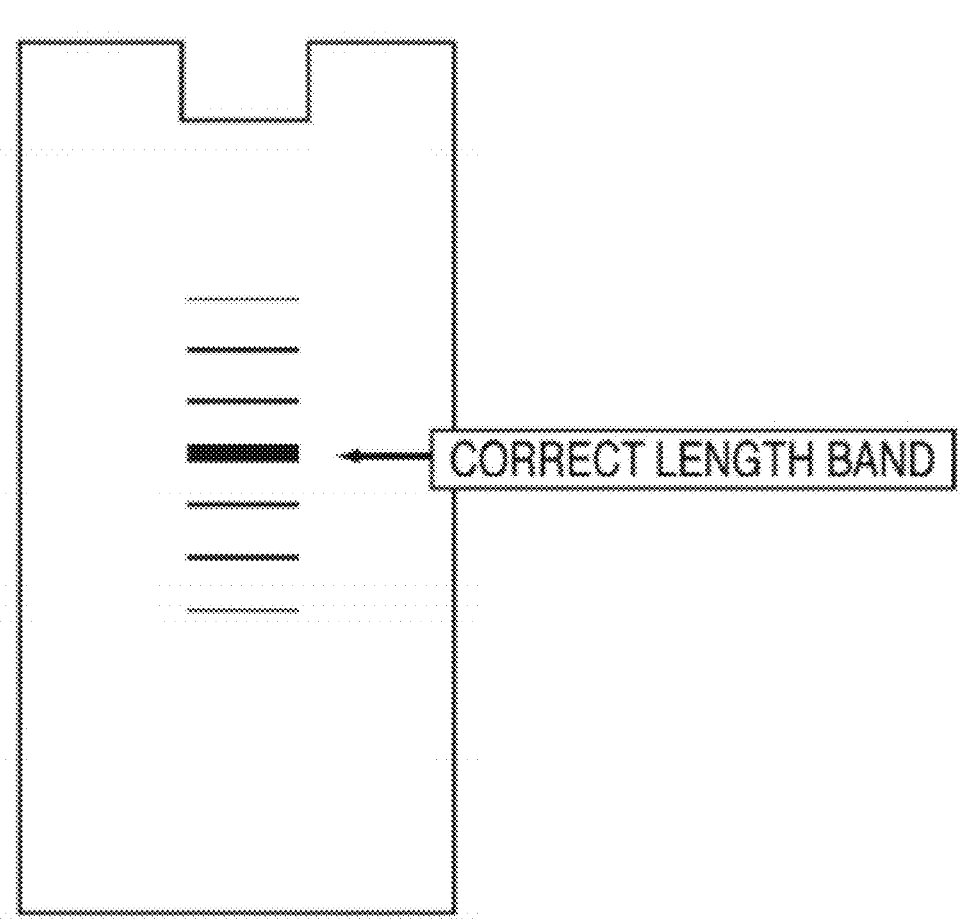
FIG. 3 shows cartoon of page gel after answers are formed. The arrow points to the correct size band that will be excised.

1. The DNA strands are separated by their lengths using gel electrophoresis and all 220-mers are removed from the gel (FIG. 3). Answer sequences that are too short or too long are either missing cities or have multiple copies of the same city; they are thus removed.

Figure 4B:
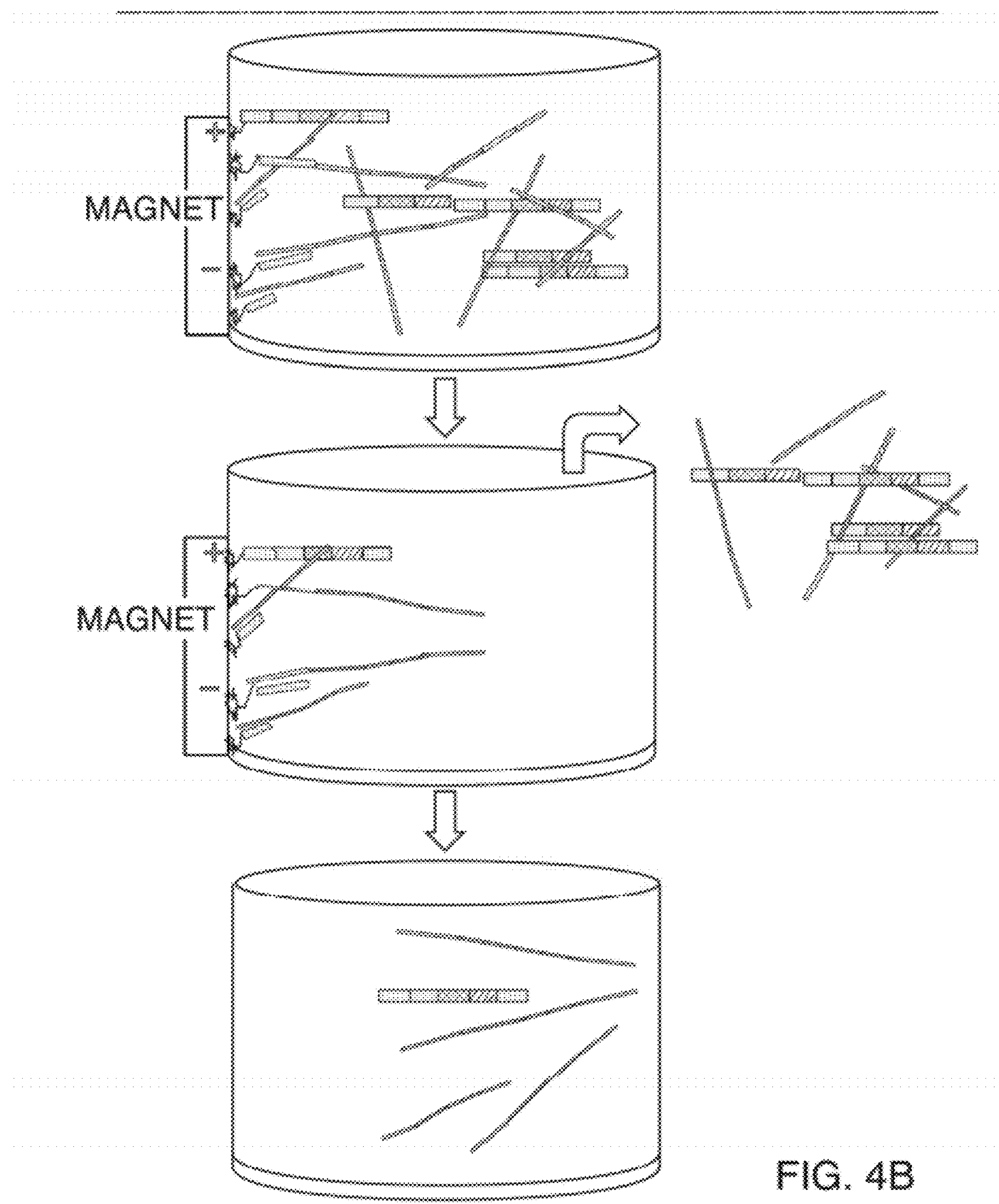
FIG. 4 shows the procedure used to purify out any solutions that have visited the same city multiple times.

2. Answer sequences are sequentially probed with the DNA complement to a city sequence tethered to magnetic beads; in this case, 10 sequential probes for each of the 10 cities (FIG. 4). This removes answer sequences that lack a city sequence.

Step 4: Determine Abundance of Adjacent City Sequences to Read the Output.

Figure 5:
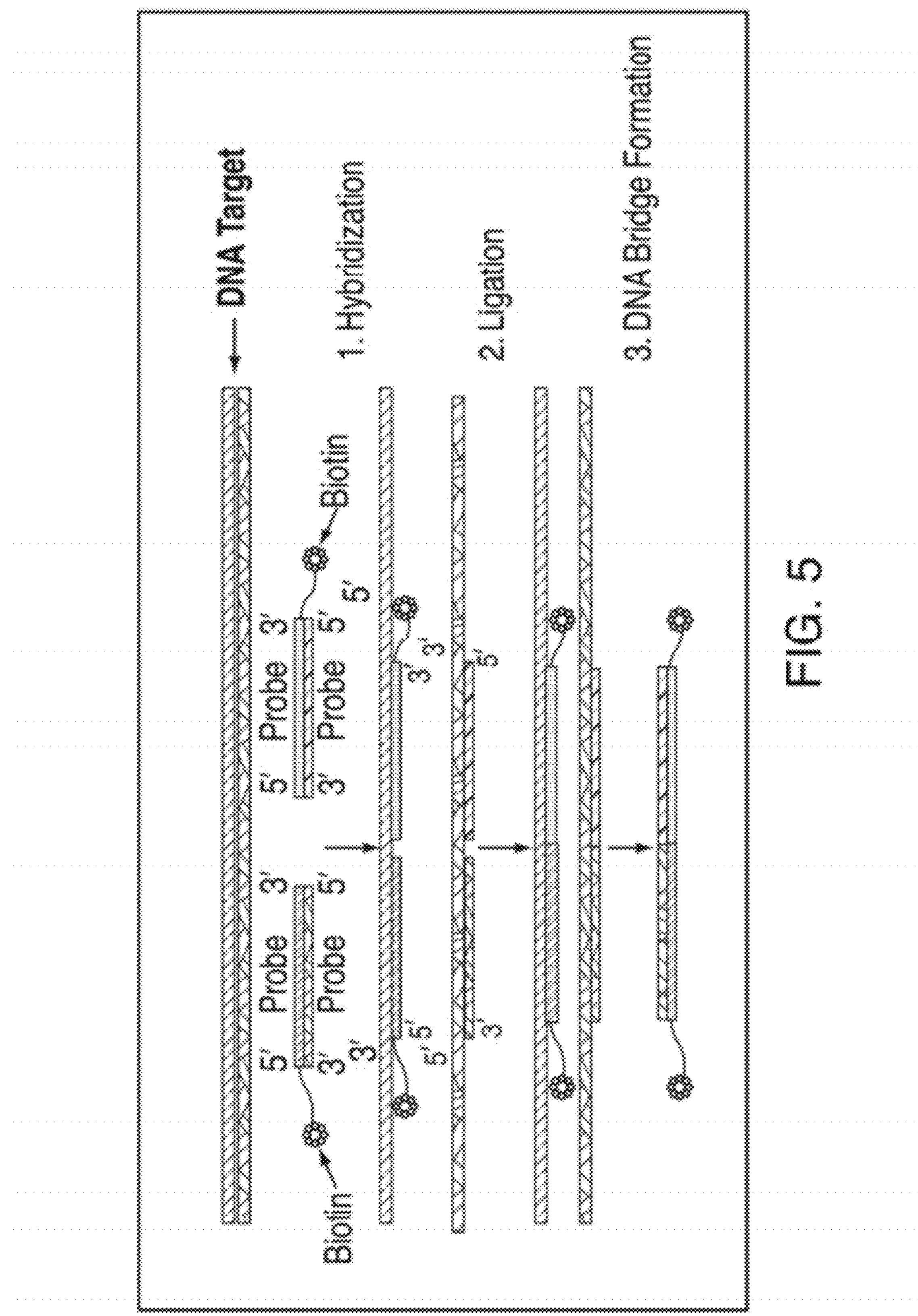
FIG. 5 shows the LCR method that is used to read out the final solution.

Biotinylated DNA probes that serve as the complement to each city sequence are added to the answer sequences to build DNA bridges via hybridization and ligation using the molecular motor methodology developed in this laboratory (See, for example, WO 2005/080603; incorporated by reference herein in its entirety). The 3' biotinylated probe for city A is added to the answer solution first with the 5' biotinylated probe for City B, followed by ligation to build DNA bridges (FIG. 5). Quantitation of these bridges provides information concerning how often City A precedes City B in the answer set. This is repeated for City A with all of the other cities, and ultimately for all possible city pairings.

EXAMPLE 2

Application of the General Method

A set of 10 unique 20-mer city sequences (input polynucleotides) was designed to represent each city and synthesized by Invitrogen Corporation. An additional 90 pathway sequences (connection polynucleotides) were synthesized containing all possible combinations of the complementary sequences to join any two city sequences together. The polynucleotide sequences were designed to minimize cross hybridization, self-assembly and secondary structure formation and retain very similar thermal properties (melting temperature, in range of 61.3 to 61.8° C.) and GC content (25-30%). However, we used start and end city sequences with an additional "GC cap" (string of G or C residues) that raised the PCR™ of these sequences to 68-72° C. to further minimize secondary structure formation and inappropriate insertion of the staring and/or ending city sequence into the middle of the solution.

The yields of the synthesis for the DNA oligos were used to determine the distance matrix that defined the problem to be solved (ie: the weight assigned to each connection polynucleotide and pathway sequence is based on its synthesis yield, to ensure that we solved a randomly generated problem. Traditionally, the traveling salesman problem is constrained to distance matrices that fall in 2 or 3 dimensions. However, this reduces the complexity of the problem and does not test the full capability of the DNA computer. Thus, the distance matrix we chose to solve was not constrained, and solving it suffices to show that the technique can be used to solve any problem of lesser complexity. The distance matrix used is shown in Table 1.

TABLE 1

| Distance Matrix | | | | | | | | | | |
|---|---|---|---|---|---|---|---|---|---|---|
| | A | B | C | D | E | F | G | H | I | J |
| A | ** | 55.2 | 34.05 | 31.75 | 53.85 | 39.95 | 36 | 39.9 | 36.55 | 52.6 |
| B | 63.95 | ** | 54.25 | 54.95 | 72.6 | 45.05 | 71.65 | 50.55 | 52.75 | 52.15 |
| C | 51.35 | 47.6 | ** | 41.45 | 39.8 | 57.8 | 55.2 | 32.75 | 34.85 | 37.05 |
| D | 46.65 | 46.25 | 54.6 | ** | 49.4 | 45.55 | 55.9 | 52 | 57.35 | 54.6 |
| E | 49.9 | 39.1 | 42.65 | 52.4 | ** | 25.9 | 39.85 | 38.85 | 37.95 | 33.1 |

TABLE 1-continued

| Distance Matrix | | | | | | | | | | |
|---|---|---|---|---|---|---|---|---|---|---|
| | A | B | C | D | E | F | G | H | I | J |
| F | 59.7 | 49.15 | 47.8 | 56.9 | 58.05 | ** | 48.05 | 46.6 | 48.4 | 47.7 |
| G | 51.25 | 36.7 | 43.95 | 43 | 42.45 | 40.25 | ** | 64.2 | 47.8 | 46.95 |
| H | 58.1 | 35.85 | 53.7 | 45.05 | 47.3 | 43 | 84.25 | ** | 42.8 | 41.9 |
| I | 52.9 | 38.2 | 40.35 | 33.45 | 36.5 | 65.2 | 35 | 29.7 | ** | 30.95 |
| J | 60.05 | 39.1 | 40.65 | 55.75 | 41 | 41.1 | 45.1 | 58.65 | 43.95 | ** |

for example, in row "a", under column "b" the number is 55.2; in row "b" under column "a" the number is 63.95; the former represents a-b connection polynucleotide while the latter represents b-a connection polynucleotide.

b. Hybridize City and Pathway DNA Sequences Based on a Distance Matrix Between Cities.

We set an approximate 10:1 (city:linker) concentration ratio for hybridization and ligation reactions. This ensures city sequence concentrations are saturated concentrations compared to the pathway sequences, while pathway sequence concentrations are limiting and are varied in a manner that any potential linking between any pair of cities is totally dependent upon concentration of the corresponding linker. Table 1 shows concentration differences for all linkers that were used for solving 10-city problem.

The differences in linker concentrations from the vendor were used to define the problem, with the lowest concentration being 25.3 ng/ul and the highest one being 84.5 ng/ul. As will be understood by those of skill in the art, any other parameter applicable to a given problem can be used for determining the weight assigned to the connection polynucleotides (pathway sequences).

The initial solution pool was generated through hybridization and ligation adapted from Adleman's (1994) protocol. In addition, we developed and performed a two-step protocol to generate the initial solution pool. First, initial hybridization/ligation was conducted in mixture in the absence of the ending city sequence and all potential linkers to the ending city. This greatly reduced formation of shorter solutions, thus improving the hybridization/ligation efficiency. Second, the hybridization/ligation was allowed to continue with the addition of fresh ligase, the ending city sequence and corresponding linkers.

c. Removal of Answer Sequences Lacking a City Sequence.

1. Isolation of Solutions

Following ligation, PCR amplifications of ligation products at a hybridization Tm of 68-70° C., purification of the ligation products was carried out by denaturing polyacrylamide gel electrophoresis, with the following modifications to avoid smearing due to secondary structure formation:

(1) Including of 8 M urea and 30% formamide as denaturants in the gel;

(2) Adjusting the speed of gel polymerization by chemical and photochemical catalysis. We used 20 ml liquid acrylamide and then added 100 μl 10% pyrophosphate, and polymerized the gel under a light; and (3) Immersing the PAGE device in a 60-65° C. water bath during electrophoresis.

By utilizing this protocol, 230mer DNA bands were clearly resolved, and further PCR purification using the 230-mer DNA template extracted from the excised PAGE gel generated sharp DNA bands with the desired, 230-mer length. This confirms that we collected the 230-mer, 10-city solutions (ligation products or solutions) with correct starting and ending cities.

2. Probing Solutions with the DNA Compliment to a City Sequence Tethered to Magnetic Beads.

Magnetic-bead affinity purifications of the 230-mer solutions using biotinylated oligo probes containing complementary sequence for each city was carried out to ensure every city was visited once and only once. This procedure removed answer sequences that were missing any one city. To implement magnetic affinity purifications, a ssDNA (single stranded) solution pool was generated by PCR amplifying the 230-mer solutions using 3'-biotinylated primer. Biotinylated DNA of complementary sequences to each city was attached to streptavidin-functionalized magnetic beads. The amplified solution pool was then incubated with magnetic beads bound to the complimentary sequence of City A and DNA strands containing City A sequences were removed with a magnet and the remaining DNA was washed away.

Answer sequences were then recovered from the beads by a chemical denaturing protocol devised to obtain the screened ssDNA solution without the biotinylated city probe. For chemical denaturing, 50 ul of 0.1N NaOH were used followed by an addition of 7 ul of 1M HCl for neutralization.

Using this protocol, we found that after all 10 cities had been screened by magnetic-bead affinity purification, a sharp 230-mer DNA band of the answer solutions remained.

d. Determine Abundance of Adjacent City Sequences to Read the Output.

Figure 6:
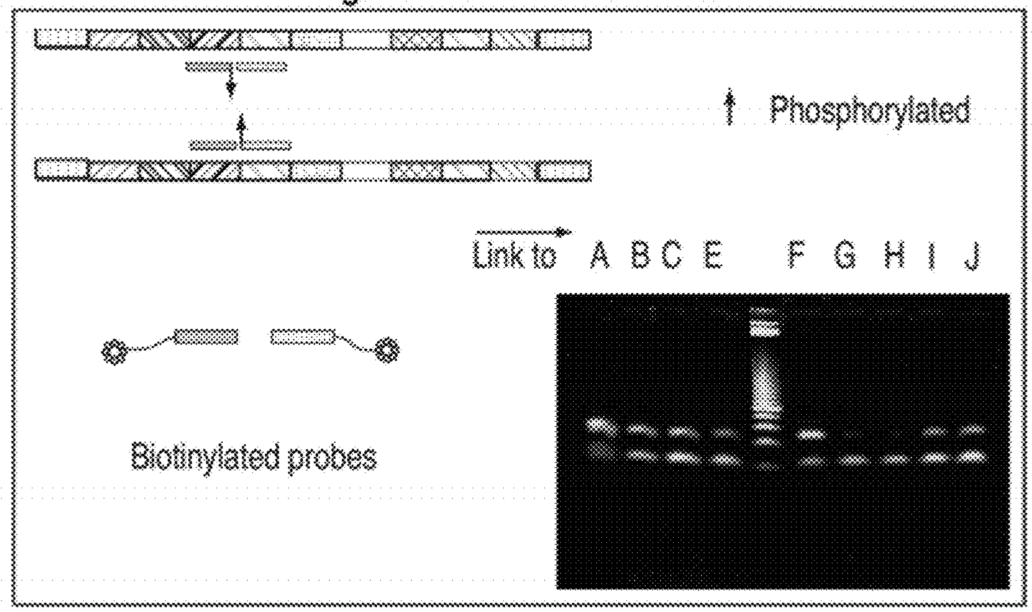
FIG. 6 is a PAGE profile of ligation chain reaction product. For each LCR, the 230-mer DNA solutions plus two pairs of probes were included. If the solutions are readout using ATPase motor detection technique, two probes need to be biotinylated.
Figure 6:
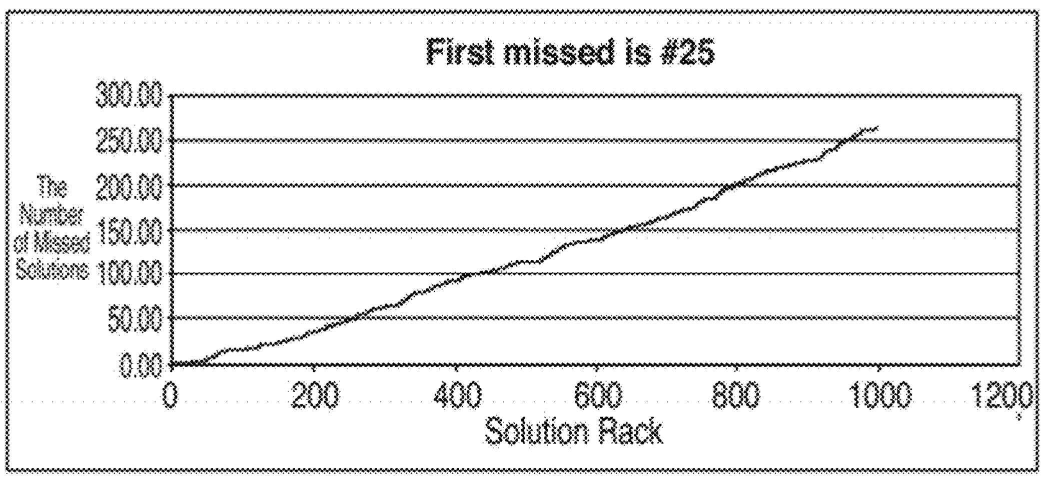

The techniques developed to produce the solution set were efficient enough to allow us to use a combination of PAGE and ligation chain reaction (LCR) techniques (See, for example, WO 2005/080603) to read the answer of the problem computed. The 3'biotinylated probe for city A was added to the answer solution first with the 5'biotinylated probe for City B, followed by ligation to build DNA bridges (FIG. 6). Quantitation of these bridges provides information concerning how often City A precedes City B in the answer set. This is repeated for City A with all of the other cities, and ultimately for all possible city pairings. LCR products were profiled on a PAGE gel and the relative abundance of each potential pairing of cities was measured as total density using the UVP GDS-8000 BioImaging system.

The concentration of each probe was measured in triplicate using the NanoDrop method, and a saturating concentration for each probe was established. This ensures the yield of LCR product for a given link between two cities will be attributed to abundance in the answer solution. FIG. 6 inset shows a typical LCR profile of PAGE gel which illustrates probabilistic links between City D and the rest other 9 cities.

Quantitative determination of the yield of LCR product in each lane of the gel was accomplished by: (1) measuring the total density of the upper DNA band (the LCR product) and the lower DNA band (the PCR probes); (2) measuring total density of the 100-mer band (the brightest one) from DNA ladder; (3) normalizing the total density of LCR product and probes against the 100-mer DNA ladder; and (4) determining the ratio of the normalized total density of PCR product over the normalized total density of PCR probe. These ratios were then stored in a matrix called R, the elements of which represent a global measure of the amount of city pairings that exist in the solution set.

The matrix formed from the city pairings as the result of the gel analysis is shown in Table 2.

TABLE 2

Matrix formed through the LCR gel read out.

| | A | B | C | D | E | F | G | H | I | J |
|---|---|---|---|---|---|---|---|---|---|---|
| A | *** | 0.30 | 0.16 | 0.26 | 0.23 | 0.26 | 0.47 | 0.24 | 0.00 | 0.08 |
| B | 0.11 | *** | 0.27 | 0.09 | 0.14 | 0.15 | 0.17 | 0.19 | 0.17 | 0.06 |
| C | 0.16 | 0.27 | *** | 0.10 | 0.16 | 0.13 | 0.13 | 0.18 | 0.13 | 0.09 |
| D | 0.09 | 0.05 | 0.05 | *** | 0.01 | 0.07 | 0.06 | 0.06 | 0.10 | 0.06 |
| E | 0.17 | 0.17 | 0.07 | 0.15 | *** | 0.19 | 0.05 | 0.09 | 0.02 | 0.15 |
| F | 0.16 | 0.03 | 0.11 | 0.10 | 0.29 | *** | 0.04 | 0.10 | 0.11 | 0.14 |
| G | 0.06 | 0.01 | 0.06 | 0.00 | 0.00 | 0.01 | *** | 0.00 | 0.05 | 0.08 |
| H | 0.03 | 0.00 | 0.03 | 0.00 | 0.00 | 0.01 | 0.03 | *** | 0.14 | 0.10 |
| I | 0.11 | 0.08 | 0.09 | 0.10 | 0.04 | 0.07 | 0.03 | 0.04 | *** | 0.23 |
| J | 0.12 | 0.09 | 0.17 | 0.18 | 0.14 | 0.10 | 0.04 | 0.11 | 0.2 | *** |

***indicate paths that are nor contained in the subset generated

This table redefines the TSP, from one that had 3.3 million possible solutions, to one with ~250,000 solutions. A conventional computer with a standard brute force algorithm was used to find the optimal answer of the 250 k solutions generated.

The number of possible solutions in R is substantially less than in the original distance matrix calculated by a conventional computer because the total number of DNA molecules used in the calculation was insufficient to generate all of the possible answers. The number of possible solutions is limited by those rows and columns that have the fewest possible transitions, where a “transition” means moving from one city to another. Each row or column that has fewer than 9 transitions limits the number of degrees of freedom (ie: how many other cities it can directly connect to) that any path may travel. For example, H may only be traveled to from I or J, and thus it has a degree of freedom of 6. The zeros in the above matrix mean that a particular road does not exist, thus it cannot be traveled; thus only when there is a nonzero value in the matrix, can you move from one city to another. To find the maximum number of potential solutions, we begin with the path that has the smallest degree of freedom and work up from there. In this case the number of possible solutions can be calculated by taking the minimum of the lowest degree of freedom and the number of remaining cities to move to. In this way we determined that the matrix generated by the DNA computer has at most $(7*7*7!) \approx 246,960$ answer sets, or about 6.8% of the possible solutions of the original problem. Thus, our DNA computer reduced a problem with 3.3 million possible solutions to one with about 246,960.

The design of our DNA computer is based on the hypothesis that when the amount of DNA city and pathway sequences used for the computation is insufficient to generate all possible answers, the subset of possible answers generated will be the most probable, and hence, include the optimal solution. In so doing, the DNA computation would serve to reduce the problem to one that has a searchable number of solutions by a conventional computer. We were able to test this hypothesis using the computational results in R because the number of solutions to the 10 city problem was small enough to be searched by a conventional computer.

Using a conventional computer to perform a brute search of all possible solutions, the optimal solution was found to be AFEJBCDIHGA. The answer set determined by the DNA computer included the correct solution. Conventional computing was then used to determine the best 1000 answer solutions, rank them in order of best to worst. The answer solutions from the DNA computation were then examined to identify which city pairings were not contained in the subset of solutions generated by the DNA computer. The DNA computer successfully generated the 24 most optimal answers. The first answer not included in the answer set was the $25^{th}$ most optimal. The number of answers excluded by the DNA computer increased proportionately to the decrease in optimality. These results demonstrate that our DNA computer has successfully computed the 10 city traveling salesman problem.

EXAMPLE 3

Solving a 15 City Traveling Salesman Problem

In this example, manageable amounts of DNA are used to solve a 15-asymmetric traveling salesman problem (TSP), the largest problem solved by molecular computing to date. As discussed above, the TSP is to find the optimal path between all desired cities, starting and ending at the same city and visiting each city once and only once. The methods herein exploit the truly random molecular process of Brownian motion inherent in molecular interactions to generate an optimal subset of answers. A similar process is not possible using in silico computers since truly random samples cannot be generated by deterministic circuits.

Concentration control was used to implement a probabilistic computation to identify the optimal path for a fully random, connected, asymmetric 15-city TSP. When concentration of the pathway DNA is used to encode optimality, the answer population is symmetrically distributed where the mode and mean correspond to the optimal answer. Generating a subset of answers is equivalent to taking a random sampling of the population where the mean of the population is related to the mean of the sample using the classic relation: μ=Sample Mean±error. The error can be estimated from the standard deviation of the sample divided by the square root of the sample size. In this case the sample size is the number of molecules that form correct answers to the problem (i.e. answers with one and only one copy of each city). Amplification of the correct solutions allows the sample size to be controlled. Thus, the error can be controlled to generate a sample mean to within any desired confidence interval of the mean of the population. Consequently, the number of possible answers to the problem can exceed the molecules in the reaction, thereby allowing computations of large problems with manageable amounts of DNA. As will be understood by those of skill in the art based on the teachings herein, each problem will have a different range over which inspection of the gel will be sufficient to get see the answer, and we have not determined what the bounds are for the problems we solved)

Table 3 shows the distance matrix that defines a specific problem. Each letter represents a different city in the TSP and city A serves as the starting and ending point. The experiments to implement the algorithm were divided into four steps:

Step 1: A set of unique DNA sequences was created for each city and binary pathway.

Step 2: City and pathway DNA sequences were hybridized based on the distance matrix.

Step 3: Solutions that did not satisfy the TSP requirement were removed.

Step 4: The abundance of adjacent city sequences was determined to read out the optimal solution set.

Figure 8:
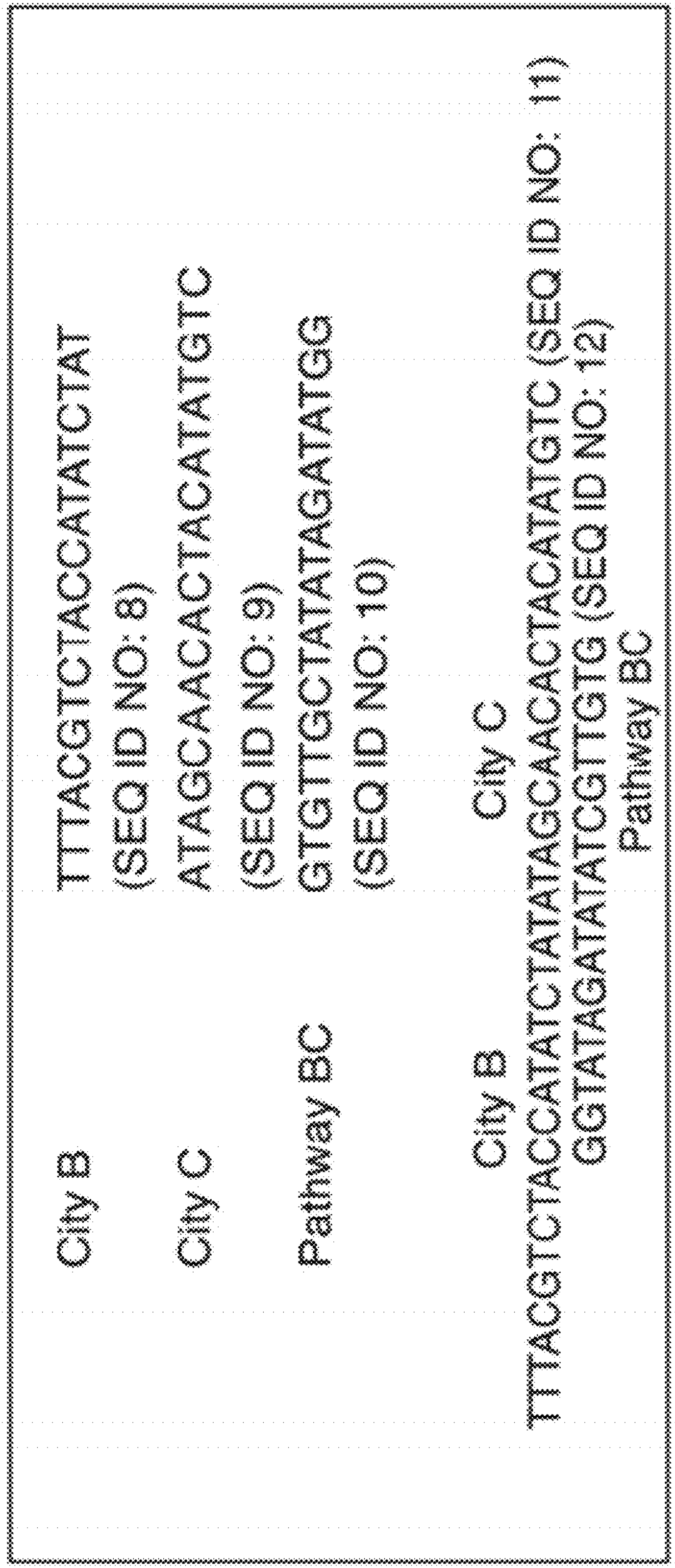
FIG. 8 shows an example of city B, city C and pathway BC that connects them.

To implement Step 1 of the algorithm, each city was associated with a synthetic 20-mer sequence of DNA. They were chosen to minimize the cross hybridization, with melting points varied from 60.6 to 62° C. and GC content from 20% to 35%. For each pathway that connected two different cities, a 20-mer DNA was created such that hybridization of the pathway sequences occurs between the first half of one city and the second half of another. FIG. 8 gives an example of city B, city C and pathway BC that connects them. This construction allowed the set of city sequences to be linked sequentially in all possible combinations to form long solution strands upon addition of ligase. Answers were formed by combining 100 pmols of each city sequence, 100 pmol of pathways from $A_{start}$→B, B→C, C→D, . . . , N→O, O→$A_{end}$, and 1 pmol of all other pathways in distilled water. The solution was heated to 92° C. for 4 min, cooled at 1° C./min to 4° C., then incubated at 8° C. for ~16 h after addition of T4 ligase (5 Weiss Units), 20 mM DTT, and 10 mM ATP. This treatment was repeated prior to a final addition of T4 ligase (5 Weiss Units), 20 mM DTT, and 10 mM ATP followed by incubation for 16 h at 8° C.

Fourteen unique DNA 20mers were designed with similar melting temperatures and assigned to each city designated B-O. Two city A sequences were designed to serve as the starting and ending point, each a 40mer with a higher GC content than cities B-O so they could serve as PCR primers. Intercity pathway 20mers hybridized with the first and last halves of cities to assemble city strands in a sequential manner which correlates to a particular city order. Pathways were added in amounts that varied relative to the efficiency of that path. Low and high efficiency paths were added at 1 and 100 pmol respectively, where high efficiency paths bridged cities in alphabetical order.

In addition, two sequences that represented starting city $A_s$ and ending city $A_e$ separately were designed to replace the single city A sequence (FIG. 9). The second-half and the first-half of the original city A sequence were used in the new starting and ending sequences respectively. Each half of the original was extended by unique 10-mer sequences with 100% GC content to raise the melting temperature and eliminate non specific annealing during PCR amplification. An additional 5-mer GC cap was added to prevent two point cities from being inserted in the middle of the solutions. To further reduce formation of incomplete solution sequences step 2 was performed in two stages. First, hybridization/ligation was initiated in the absence of the ending city $A_e$ and all pathways directed to $A_e$ for a period sufficient to enable strand ligation. Second, the reaction was continued by adding fresh ligase, the ending city sequence, and corresponding pathways to produce the complete final solutions that start and end with the same city.

To implement Step 3, the hybridization/ligation products of Step 2 were purified by PCR amplification using the 5'-starting and the 3'-ending city primers. The PCR primers were designed to complement unique sequences of $A_s$ and $A_e$. Consequently, only those molecules encoding routes that begin and end with the assigned city were able to be amplified. The PCR products were profiled on a denaturing polyacrylamide gel, and the 330-mer band corresponding to DNA encoding round-trip routes entering exactly 16 cities (25-mer city $A_s$ and $A_e$, 20-mer other 14 cities) were excised (FIG. 10 (*a*)(A)). These PCR amplification and gel purification procedures were repeated several times to enhance the purity of target DNA (FIG. 10 (*a*)(B)). Ligation products were separated by a 6% denaturing PAGE gel with 8.5 M urea and 30% formamide, (acrylamide:bisacrylamide, 29:1) in 100 mM Tris-Cl, pH 8.3, 83 mM boric acid, and 2 mM EDTA at ~55° C. under 8 V/cm. Polymerization speed of the gel was controlled using chemical and photochemical catalysis to increase resolution. Electrophoresis was performed at ~65° C. The 340mer band was collected from the gel using a Qiagen gel extraction kit. Answer sequences containing $A_{start}$ and $A_{end}$ were purified by magnetic affinity, followed by PCR amplification in a 50 μL reaction mixture containing 10 mM Tris-HCl, pH 8.3, 50 mM KCl, 1.5 mM $MgCl_2$, 0.001% gelatin, 200 μM each dNTP, 0.4 μM of each of the $A_{start}$ and $A_{end}$ primers, a 1:100 ratio of Bst and Taq DNA polymerase, and 0.1-0.2 μg DNA template. The PCR reaction occurred in a PJ2000 DNA thermal cycler programmed for a hot start at 94° C. for 2.5 min followed by 35 cycles of 94° C. for 0.5 min, 70° C. for 35 sec, and 72° C. for 30 sec, concluded by 3 min at 72° C.

To ensure each 330-mer strand exactly contained all the cities, the multiple purified DNA sequences were probed by biotin-avidin magnetic beads system. This was accomplished by first incubating the products with the complementary sequences to city B that were conjugated to magnetic beads. Using a magnetic separator, only the strands that contained the city B sequence (and hence code routes that enter city B at least once) were retained by hybridization to the immobilized probes. This process was repeated successively with every city and the final products were amplified by PCR and run on a gel. The single bright band in FIG. 10 (*a*)(C) represented the final separated DNA solutions that start and end at city A, and also include each of the other 14 cities once and only once. It is note worthy that this band contained not only the optimal TSP solution in the largest abundance but also other correct but suboptimal Hamiltonian loops (FIG. 10(*b*)). The PCR products were profiled on a 6% denaturing PAGE gel as described above. The amplified solution was filtered using sequential magnetic affinity purification for each of the cities B-O.

To implement Step 4, the final answers pool from Step 3 was detected with pairs of probes that were complementary to two selected cities in all possible combinations. When the two cities were adjacent in a specific order, the complementary probes would become covalently linked through the ligation chain reaction (LCR). LCR was performed with equal saturated amounts of probe to ensure that the yield of LCR product for a given link between two cities was limited by the abundance of the corresponding answers. In the 15-city problem, 210 reactions were run for each possible pairing, and the products were profiled on PAGE gels (FIG. 9). The lower bands in each lane corresponded to 20-mer DNA probes that were not ligated during LCR. The upper bands corresponded to the 40-mer composed of the ligated probes and thus, indicated the abundance of that ordered city pair in the answers pool. The LCR reaction mixture contained 10× buffer, 5 μL target DNA (10 ng), 40 units Taq ligase (NEB), and 400 nM of each of 4 probes in a 50 μL final volume. The 4 probes included two city sequences and their complements. For each reaction, one sequence of each pair was phosphorylated (city1:P*-city2 and P*-compliment1:compliment2) to ensure that ligation could only occur if city1 immediately preceded city2. The LCR was initiated by heating the solution to 94° C., for 2.5 min, following by 25 cycles with each cycle consisting of 94° C. for 25 sec, 41° C. for 35 sec, and 45° C. for 150 sec. LCR products were profiled by on a 10% PAGE gel, (acrylamide:bisacrylamide, 29:1) in 100 mM Tris-Cl, pH 8.3, 83 mM boric acid, and 2 mM EDTA at ~55° C. under 8 V/cm. All PAGE gels were stained with ethidium bromide (1 mg/ml) for 10 min, then visualized and photographed with a UVP BioDoc-It™ UV transilluminator.

TABLE 3

Matrix for concentration ratio in the 15-city TSP

| | A | B | C | D | E | F | G | H | I | J | K | L | M | N | O |
|---|---|---|---|---|---|---|---|---|---|---|---|---|---|---|---|
| A | *** | 100 | 1 | 1 | 1 | 1 | 1 | 1 | 1 | 1 | 1 | 1 | 1 | 1 | 1 |
| B | 1 | *** | 100 | 1 | 1 | 1 | 1 | 1 | 1 | 1 | 1 | 1 | 1 | 1 | 1 |
| C | 1 | 1 | *** | 100 | 1 | 1 | 1 | 1 | 1 | 1 | 1 | 1 | 1 | 1 | 1 |
| D | 1 | 1 | 1 | *** | 100 | 1 | 1 | 1 | 1 | 1 | 1 | 1 | 1 | 1 | 1 |
| F | 1 | 1 | 1 | 1 | *** | 100 | 1 | 1 | 1 | 1 | 1 | 1 | 1 | 1 | 1 |
| F | 1 | 1 | 1 | 1 | 1 | *** | 100 | 1 | 1 | 1 | 1 | 1 | 1 | 1 | 1 |
| G | 1 | 1 | 1 | 1 | 1 | 1 | *** | 100 | 1 | 1 | 1 | 1 | 1 | 1 | 1 |
| H | 1 | 1 | 1 | 1 | 1 | 1 | 1 | *** | 100 | 1 | 1 | 1 | 1 | 1 | 1 |
| I | 1 | 1 | 1 | 1 | 1 | 1 | 1 | 1 | *** | 100 | 1 | 1 | 1 | 1 | 1 |
| J | 1 | 1 | 1 | 1 | 1 | 1 | 1 | 1 | 1 | *** | 100 | 1 | 1 | 1 | 1 |
| K | 1 | 1 | 1 | 1 | 1 | 1 | 1 | 1 | 1 | 1 | *** | 100 | 1 | 1 | 1 |
| L | 1 | 1 | 1 | 1 | 1 | 1 | 1 | 1 | 1 | 1 | 1 | *** | 100 | 1 | 1 |
| M | 1 | 1 | 1 | 1 | 1 | 1 | 1 | 1 | 1 | 1 | 1 | 1 | *** | 100 | 1 |
| N | 1 | 1 | 1 | 1 | 1 | 1 | 1 | 1 | 1 | 1 | 1 | 1 | 1 | *** | 100 |
| O | 100 | 1 | 1 | 1 | 1 | 1 | 1 | 1 | 1 | 1 | 1 | 1 | 1 | 1 | *** |

A carefully controlled concentration matrix replaced the previous random fully connected one, guaranteeing that one Hamiltonian path is clearly optimal compared to others. This path was selected to be ABCDEFGHIJKLMNOA, by adding pathway sequences i.e. AB, BC, CD, etc. at concentration 100 fold greater than pathway sequences that would lead to sub-optimal answers (Table 3). It is note worthy that due to the purposely assigned optimal path and corresponding concentration control, this experiment provided a test of the feasibility of the method rather than a blind search for an unknown solution as was done in the 10-city TSP.

Another important modification of the protocol for the 15-city problem computing was the enhancement of purity of oligonucleotides used in the hybridization/ligation reaction. The initial set of 20-mer sequences representing cities and pathways were ordered from Invitrogen Inc., with approximately 70% purity. To accomplish the ligation reaction, those sequences, except for the starting city $A_s$ and all pathways directed from $A_s$ to subsequent pathways had to be phosphorylated so that phosphodiester bonds could be synthesized between adjacent sequences upon ligation. Therefore, three factors were identified that affect efficiency of the answer generation step: 1) the purity of initial oligonucleotides; 2) the efficiency of phosphorylation reaction; 3) the efficiency of ligation reaction. If the numbers were 70%, 75%, 50% respectively, the probability of producing a whole strand would approach zero ($0.7\times0.75^{15}\times0.5^{14}=5.7\times10^{-7}$). To increase the yield of complete answer sets, all initial oligonucleotides were purified before and again after phosphorylation.

High-performance liquid chromatography (HPLC) coupled to indirect ultraviolet detection was used for DNA purification. For oligonucleotide purification, each DNA sample representing a city or pathway was injected into the buffer flow path of the HPLC system. The positively charged molecules in solution could associate with DNA sequences that have the negatively charged phosphate backbone. This entire entity behaved as a typical hydrophobic molecule and was attracted to the neutral (hydrophobic) beads located in the separation cartridge. The wash buffer containing acetonitrile (ACN) was used to break the hydrophobic interaction between the DNA complex and the cartridge. As the ACN concentration increased over time, bridging capabilities of the positive ions decreased and the DNA fragments were released from the cartridge. The UV detector measured the absorbance of the DNA fragments that passed through it. Only the product corresponding to the main peak was collected and condensed to high stock concentration by the thermal centrifuge device. The purity of oligonucleotides prepared for further reaction was improved significantly.

The HPLC system was also used to separate phosphorylated DNA. Due to the addition of phosphate groups, phosphorylated products are able to elute earlier from the cartridge than the un-phosphorylated molecules.

The efficiency of the ligation reaction was improved by modifying the hybridization/ligation reaction into a three-day protocol. The reaction mixture was first heated to 92° for 4 minutes, following a programmed cooling at 1° per minute until 8°, then maintained overnight. On the second day that heating-cooling procedure was repeated and the overnight incubation was completed with additional fresh ligase and reaction buffer. On the last day more fresh ligase and buffer were added into the solution for overnight incubation. This method largely fostered the formation of answer sequences long enough that could represent the correct answers.

Figure 10B:
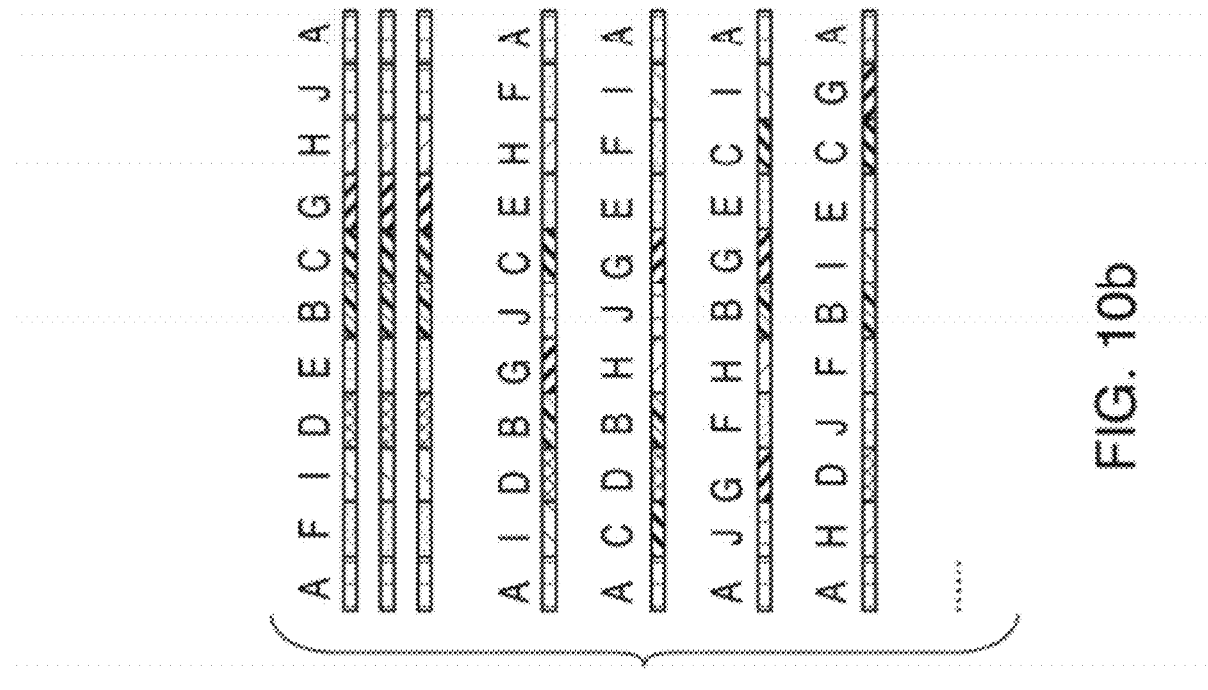
FIG. 10(*a*) (A-C) is an exemplary denaturing polyacrylamide gel for purification of bands corresponding to DNA encoding round-trip routes entering exactly 16 cities (25-mer city $A_s$ and $A_e$, 20-mer other 14 cities).
Figure 10A:
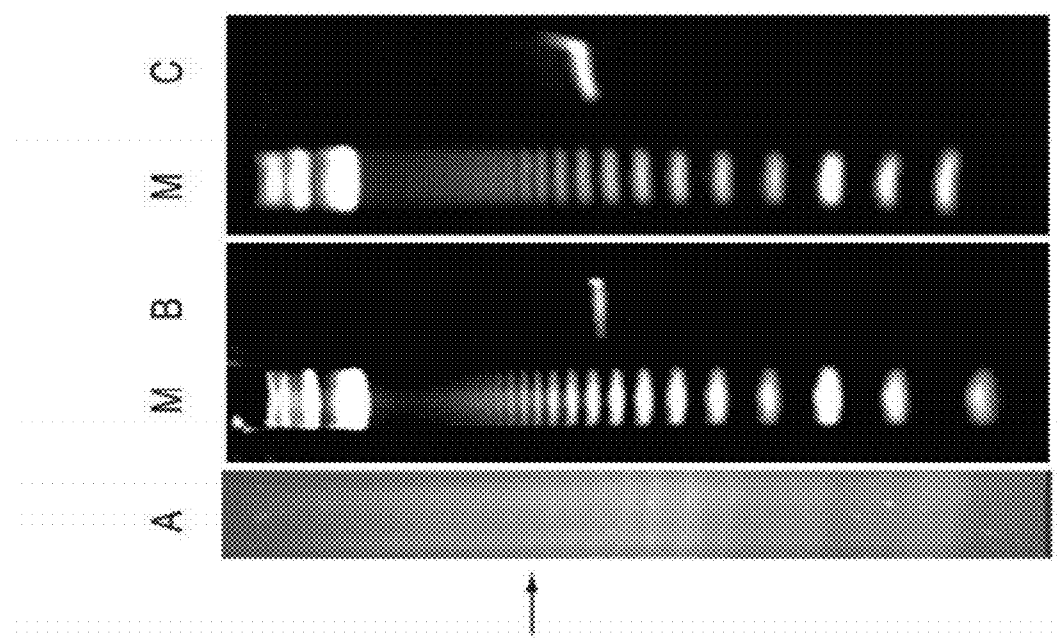

The answer readout profile of the 15-city problem is showed in FIG. 10. The pathways contained in the optimal solution were obvious in each group of LCR reactions, enabling the optimal answer to be determined by inspection. The consistency between the final optimal answer calculated by DNA computing and the initial design confirms the feasibility of this modified method. Several minor bands presented at 40-mer position indicates that besides the best answer, the DNA computer also produce some suboptimal answers showing that the computer was indeed sampling the entire answer space.

In the 15-city TSP solved here, we assembled answer strands through hybridization and ligation. DNA of the correct length (340mer) was purified by PAGE, amplified, and then filtered by sequential magnetic affinity purification using the compliment to each city to ensure that each city was visited once and only once. This resulted in a population of DNA in which solutions to the 15 city problem occur in amounts proportional to their optimality. The optimal answer was determined using a series of ligation chain reactions, where each reaction tested every possible city-city ordered pair. Successful ligation resulted in a 40mer, which indicated how often one city directly preceded another. The ligation products for each ordered city pair were separated by PAGE, where each gel tested a complete set of ordered pairs where the preceding city remained constant (e.g. A→B, A→C, A→D, etc.).

Figure 11:
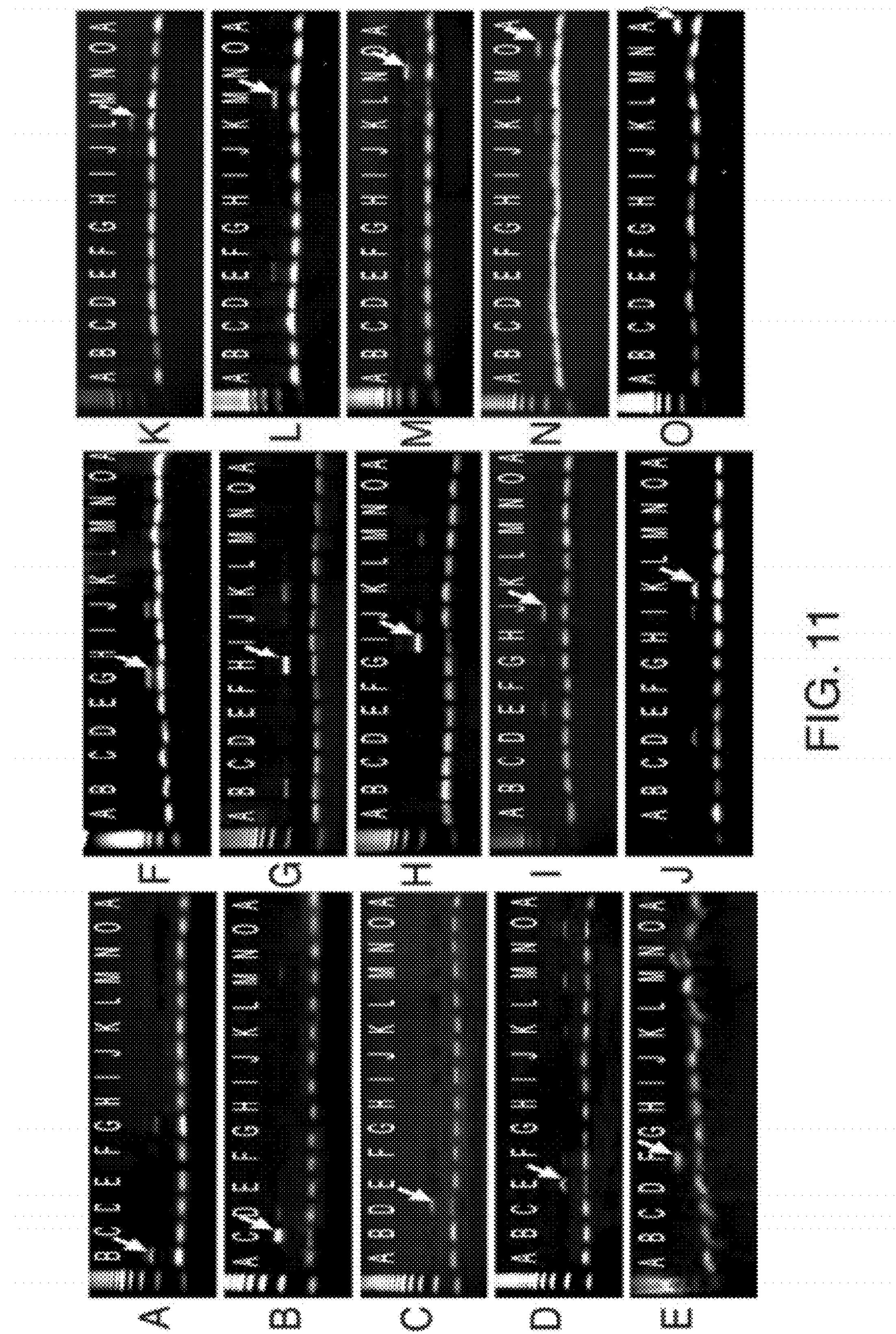
FIG. 11 (A-O) PAGE profile of 40mer LCR products for every possible city pairing. The letter on the left of each gel indicates the preceding city of the pair, where each lane tests the relative abundance of the specific city pairing in the answer sequences indicated by the letter above the lane. Arrows indicate the most abundant product band on each gel. Each lane contains excess probes, which appear as a 20mer band.

Taken together, the results of all the gels confirm that the optimal solution occurred in alphabetical order (e.g. A→B, B→C, C→D, etc.), showing that the optimal answer is easily determined by inspection (FIG. 11). Other pairings were observed in smaller abundance which indicated that the entire answer space was sampled during the computation. These results demonstrate that interactions of DNA molecules can be used to generate a random sample of a population by solving a problem with $1.3*10^{12}$ possible solutions.

Work Cited

Adleman, L. M. (1994). "Molecular computation of solutions to combinatorial problems." *Science* 266(5187): 1021-4.

Hartmanis, J. (1995). "Response to the Essays on Computational-Complexity and the Nature of Computer-Science." *Acm Computing Surveys* 27(1): 59-61.

Lee, J. Y., S. Y. Shin, et al. (2004). "Solving traveling salesman problems with DNA molecules encoding numerical values." *Biosystems* 78(1-3): 39-47.

Tanaka, F., A. Kameda, et al. (2005). "Design of nucleic acid sequences for DNA computing based on a thermodynamic approach." *Nucleic Acids Res* 33(3): 903-11.

Yamamoto, M., A. Kameda, et al. (2002). "A separation method for DNA computing based on concentration control." *New Generation Computing* 20(3): 251-261.

We claim:

1. A method for generating a distribution of optimal answers to a nondeterministic polynomial optimization problem comprising:

(a) providing n solutions comprising input polynucleotides, wherein each solution comprises identical input polynucleotides; and wherein n equals a number of data inputs in the problem to be answered, and wherein each input polynucleotide comprises an x segment and a y segment;

(b) providing z solutions comprising connection polynucleotides, wherein each solution comprises identical connection polynucleotides; and wherein z equals a number of unique connections that can be made between the different data inputs, and wherein each polynucleotide in the set of connection polynucleotides is complementary to the x segment of one input polynucleotide and to the y segment of one different input polynucleotide;

(c) combining the solutions comprising the input polynucleotides with the solutions comprising the connection polynucleotides to form a hybridization mixture, wherein the combining is done under conditions to promote formation of hybridization complexes between complementary polynucleotides, and wherein each individual connection polynucleotide is added at a concentration based on a weighted value assigned to the individual connection polynucleotide;

(d) ligating the polynucleotides that are present in the hybridization complexes to form ligation products; and (e) determining a concentration of the ligation products, wherein the ligation products present at the highest concentration represent optimal answers to the nondeterministic polynomial optimization problem.

2. The method of claim 1, wherein step (c) comprises:

(i) combining the solutions comprising the input polynucleotides only with those solutions comprising connection polynucleotides that are complementary to the x or y segment of a starting input polynucleotide to form a hybridization mixture, wherein the combining is done under conditions to promote hybridization between complementary polynucleotides to form a first hybridization complex between the starting input polynucleotide, a second input polynucleotide, and one connection polynucleotide; and (ii) combining the solutions comprising the remaining connection polynucleotides not combined in step (i) with the hybridization mixture, wherein the combining is done under conditions to promote hybridization between complementary polynucleotides, wherein the remaining connection polynucleotides are added at a concentration based on a weighted value assigned to each individual remaining connection polynucleotide.

3. The method of claim 2, wherein step (c)(ii) is repeated a desired number of times.

4. The method of claim 1, wherein step (c) comprises:

(i) combining the solutions comprising the input polynucleotides only with those solutions comprising connection polynucleotides that are complementary to the x or y segment of at least two, but less than all, of the input polynucleotides, to form a hybridization mixture, wherein the combining is done under conditions to promote formation of hybridization complexes between complementary polynucleotides, and wherein each individual connection polynucleotide is added at a concentration based on a weighted value assigned to the individual connection polynucleotide; and (ii) combining the solutions comprising the remaining connection polynucleotides not combined in step (i) with the hybridization mixture, wherein the combining is done under conditions to promote hybridization between complementary polynucleotides, wherein the remaining connection polynucleotides are added at a concentration based on a weighted value assigned to each individual remaining connection polynucleotide.

5. The method of claim 4, wherein step (c)(ii) is repeated a desired number of times.

6. The method of claim 1, wherein the input polynucleotides are present in the hybridization mixture in a saturating concentration relative to the connection polynucleotides.

7. The method of claim 1, wherein determining a concentration of the ligation products comprises determining a length of the ligation products.

8. The method of claim 1, wherein the method comprises purifying those ligation products that contain each input polynucleotide prior to determining a concentration of the ligation products.

9. The method of claim 1, wherein determining a concentration of the ligation products comprises determining an order of polynucleotides in the ligation products.

10. The method of claim 9, wherein the detecting produces a reduced distance matrix with nonzero values only for those ligation products that exist in an optimal answer set.

11. The method of claim 1, wherein the nondeterministic polynomial optimization problem is selected from the group consisting of evacuation planning, invasion response planning, supply chain problems, computer chip assembly, shortest path problems, graph theory problems, network design problems, sets and partitions problems, storage and retrieval problems, sequencing and scheduling problems, mathematical programming problems, algebra and number theory problems, and program optimization problems.

12. A non-transitory computer readable storage medium comprising a set of computer program instructions that cause a computer comprising a processor to execute all the steps in the method of claim 1.

* * * * *

SEQUENCE LISTING

<160> NUMBER OF SEQ ID NOS: 15

<210> SEQ ID NO 1
<211> LENGTH: 16
<212> TYPE: DNA
<213> ORGANISM: Artificial
<220> FEATURE:
<223> OTHER INFORMATION: Synthetic

<400> SEQUENCE: 1
ctgcgctgcg cgcgcg 16

<210> SEQ ID NO 2
<211> LENGTH: 24
<212> TYPE: DNA
<213> ORGANISM: Artificial
<220> FEATURE:
<223> OTHER INFORMATION: Synthetic

<400> SEQUENCE: 2
ctgcgctgcg cgcgcgtcgt gctg 24

<210> SEQ ID NO 3
<211> LENGTH: 16
<212> TYPE: DNA
<213> ORGANISM: Artificial
<220> FEATURE:
<223> OTHER INFORMATION: Synthetic

<400> SEQUENCE: 3
cgacgcgcgc gcagca 16

<210> SEQ ID NO 4
<211> LENGTH: 32
<212> TYPE: DNA
<213> ORGANISM: Artificial
<220> FEATURE:
<223> OTHER INFORMATION: Synthetic

<400> SEQUENCE: 4
ctgcgctgcg cgcgcgtcgt gctgctcctc ct 32

<210> SEQ ID NO 5
<211> LENGTH: 24
<212> TYPE: DNA
<213> ORGANISM: Artificial
<220> FEATURE:
<223> OTHER INFORMATION: Synthetic

<400> SEQUENCE: 5
cgacgcgcgc gcagcacgac gagg 24

<210> SEQ ID NO 6
<211> LENGTH: 40
<212> TYPE: DNA
<213> ORGANISM: Artificial
<220> FEATURE:
<223> OTHER INFORMATION: Synthetic

<400> SEQUENCE: 6
ctgcgctgcg cgcgcgtcgt gctgctcctc ctctgcgctg 40

<210> SEQ ID NO 7
<211> LENGTH: 32
<212> TYPE: DNA
<213> ORGANISM: Artificial
<220> FEATURE:
<223> OTHER INFORMATION: Synthetic

<400> SEQUENCE: 7
cgacgcgcgc gcagcacgac gaggaggaga cg 32

<210> SEQ ID NO 8
<211> LENGTH: 20
<212> TYPE: DNA
<213> ORGANISM: Artificial
<220> FEATURE:
<223> OTHER INFORMATION: Synthetic

<400> SEQUENCE: 8
tttacgtcta ccatatctat 20

<210> SEQ ID NO 9
<211> LENGTH: 20
<212> TYPE: DNA
<213> ORGANISM: Artificial
<220> FEATURE:
<223> OTHER INFORMATION: Synthetic

<400> SEQUENCE: 9
atagcaacac tacatatgtc 20

<210> SEQ ID NO 10
<211> LENGTH: 20
<212> TYPE: DNA
<213> ORGANISM: Artificial
<220> FEATURE:
<223> OTHER INFORMATION: Synthetic

<400> SEQUENCE: 10
gtgttgctat atagatatgg 20

<210> SEQ ID NO 11
<211> LENGTH: 40
<212> TYPE: DNA
<213> ORGANISM: Artificial
<220> FEATURE:
<223> OTHER INFORMATION: Synthetic

<400> SEQUENCE: 11
tttacgtcta ccatatctat atagcaacac tacatatgtc 40

<210> SEQ ID NO 12
<211> LENGTH: 20
<212> TYPE: DNA
<213> ORGANISM: Artificial
<220> FEATURE:
<223> OTHER INFORMATION: Synthetic -continued

```
<400> SEQUENCE: 12

ggtatagata tatcgttgtg                                                 20


<210> SEQ ID NO 13
<211> LENGTH: 20
<212> TYPE: DNA
<213> ORGANISM: Artificial
<220> FEATURE:
<223> OTHER INFORMATION: Synthetic

<400> SEQUENCE: 13

caattctagt tctcaacatt                                                 20


<210> SEQ ID NO 14
<211> LENGTH: 25
<212> TYPE: DNA
<213> ORGANISM: Artificial
<220> FEATURE:
<223> OTHER INFORMATION: Synthetic

<400> SEQUENCE: 14

tggcacgggc gcgcgtctca acatt                                           25


<210> SEQ ID NO 15
<211> LENGTH: 25
<212> TYPE: DNA
<213> ORGANISM: Artificial
<220> FEATURE:
<223> OTHER INFORMATION: Synthetic

<400> SEQUENCE: 15

caattctagt cccgccgccg ggtag                                           25
```